United States Patent
Hall et al.

(10) Patent No.: US 12,031,874 B2
(45) Date of Patent: Jul. 9, 2024

(54) INTEGRATED TEMPERATURE CONTROL WITHIN A DIAGNOSTIC TEST SENSOR

(71) Applicant: SureSensors Ltd., Inverness (GB)

(72) Inventors: Geoffrey Frank Hall, Ross-shire (GB); Manuel Alvarez-Icaza, Inverness (GB)

(73) Assignee: SureSensors Ltd., Inverness (GB)

( * ) Notice: Subject to any disclaimer, the term of this patent is extended or adjusted under 35 U.S.C. 154(b) by 723 days.

(21) Appl. No.: 17/040,933

(22) PCT Filed: Mar. 25, 2019

(86) PCT No.: PCT/GB2019/050839
§ 371 (c)(1),
(2) Date: Sep. 23, 2020

(87) PCT Pub. No.: WO2019/186124
PCT Pub. Date: Oct. 3, 2019

(65) Prior Publication Data
US 2021/0025763 A1    Jan. 28, 2021

(30) Foreign Application Priority Data

Mar. 28, 2018  (GB) .................... 1805043

(51) Int. Cl.
*G01K 7/02*     (2021.01)
*C12Q 1/6844*   (2018.01)
(Continued)

(52) U.S. Cl.
CPC .......... *G01K 7/021* (2013.01); *C12Q 1/6844* (2013.01); *G01N 1/44* (2013.01); *H05B 3/28* (2013.01); *H05B 2203/013* (2013.01)

(58) Field of Classification Search
CPC ........ G01K 7/021; C12Q 1/6844; G01N 1/44; H05B 3/28; H05B 2203/013
See application file for complete search history.

(56) References Cited

U.S. PATENT DOCUMENTS

| 4,004,948 A | 1/1977 | Smith |
| 4,438,291 A | 3/1984 | Eichelberger et al. |

(Continued)

FOREIGN PATENT DOCUMENTS

| CN | 101894904 | * 11/2010 |
| EP | 0794427 A1 | 9/2003 |

(Continued)

OTHER PUBLICATIONS

GSI Technologies, http://www.gsitech.com/heater-and-warming-element-printing-ptc/, Nov. 20, 2017 in 3 pages.

(Continued)

*Primary Examiner* — Alexander Satanovsky
*Assistant Examiner* — Sharah Zaab
(74) *Attorney, Agent, or Firm* — Knobbe Martens Olson & Bear, LLP

(57) ABSTRACT

The invention relates to a test sensor and a heater and thermocouple device for use in a test sensor and other assays, such as a diagnostic test sensor or strip and to a method of manufacturing a test sensor and a device and a method of conducting an assay using the test sensor or device. The invention relates to a test sensor comprising a heater and thermocouple device (100), the heater and thermocouple device (100) comprising: a substrate (10); on the substrate (10), a first layer (12) of a first conductive material of a first conductivity comprising: a first thermocouple element (14); a first connector track (16) connected to the first thermocouple element (14); a resistive heater element (20); and in which at least part of the first thermocouple element (14) is comprised of a portion of the resistive heater element (20); a second layer (22) of a second conductive material of a second conductivity comprising: a second thermocouple element (24) in contact with the first thermocouple element (14) (e.g. together with the first thermo- (Continued)

couple element (14) forming a thermocouple junction (50)); a second connector track (26) connected to the second thermocouple element (24); two heater connector tracks (36A, 36B) spaced apart and connected to respective portions of the resistive heater element (20), each on a respective side of the thermocouple elements (14, 24).

20 Claims, 11 Drawing Sheets

(51) Int. Cl.
    *G01N 1/44*           (2006.01)
    *H05B 3/28*           (2006.01)

(56) References Cited

U.S. PATENT DOCUMENTS

| | | | |
|---|---|---|---|
| 5,879,630 A * | 3/1999 | Lescouzeres | G01N 27/12 338/34 |
| 6,072,165 A | 6/2000 | Feldman | |
| 8,349,259 B2 | 1/2013 | Fujii et al. | |
| 9,786,829 B2 | 10/2017 | Grande et al. | |
| 11,369,007 B2 | 6/2022 | Coursey et al. | |
| 2003/0164365 A1 * | 9/2003 | Ito | H01L 21/67103 219/465.1 |
| 2005/0076943 A1 * | 4/2005 | Cooper | G01K 7/028 136/224 |
| 2009/0325205 A1 | 12/2009 | Fujii et al. | |

FOREIGN PATENT DOCUMENTS

| | | |
|---|---|---|
| EP | 1398997 A2 | 12/2014 |
| WO | WO 2003/048709 A1 | 6/2003 |
| WO | WO 2005/027578 A1 | 3/2005 |
| WO | WO 2005/114649 A2 | 12/2005 |
| WO | WO 2011/116303 A1 | 9/2011 |
| WO | WO 2013/130593 A1 | 9/2013 |

OTHER PUBLICATIONS

Lee et al., "Application of Screen Printing in Flexible Miniature Thermocouple Process Development", International Journal of Electrochemical Science, vol. 10 (2015) pp. 3082-3087.

Olsen et al., "The Non-Metallic Thermocouple: A Differential Temperature Probe for use in Microwave Fields" in Radio Science, vol. 14, Issue 65, (1979), pp. 81-84.

\* cited by examiner

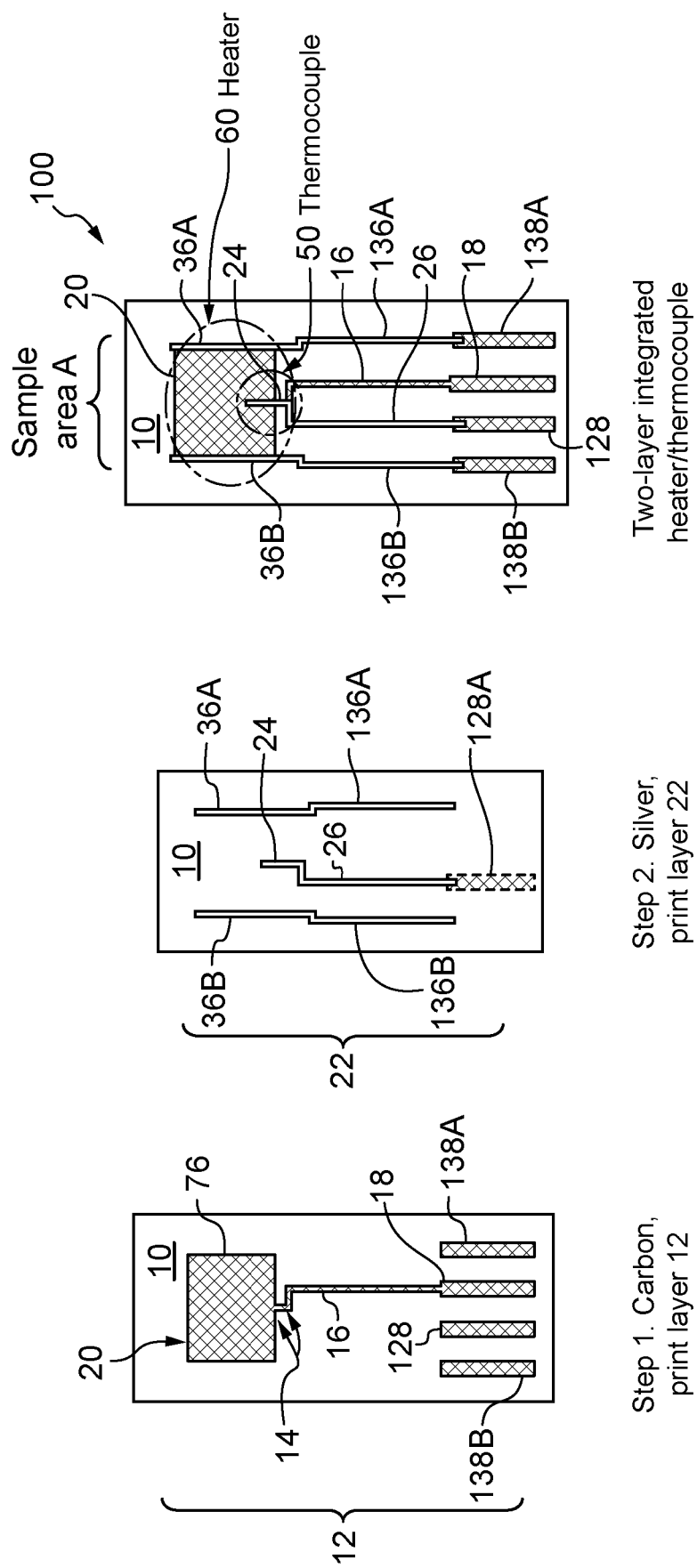

Plot of applied voltage v surface temperature of initial devices.

Plot of voltage difference across the thermocouple contacts against measured temperature of the heater element.

Plot of amplified voltage difference across the thermocouple contacts during two on/off cycles of the heater Plot of test rig display and measured strip surface temperature over time First 60 seconds of printed thermocouple output Initial response of heater Example 1: Two heating areas within single sample channel

C-C

Cross section showing sample chamber over heater/thermocouple

Example 2: Two heating areas under two separate sample areas

Example 3: Two heaters in two sample channels

Cross section showing open sample chamber over heater/thermocouple

Cross section showing sample chamber over heater/thermocouple

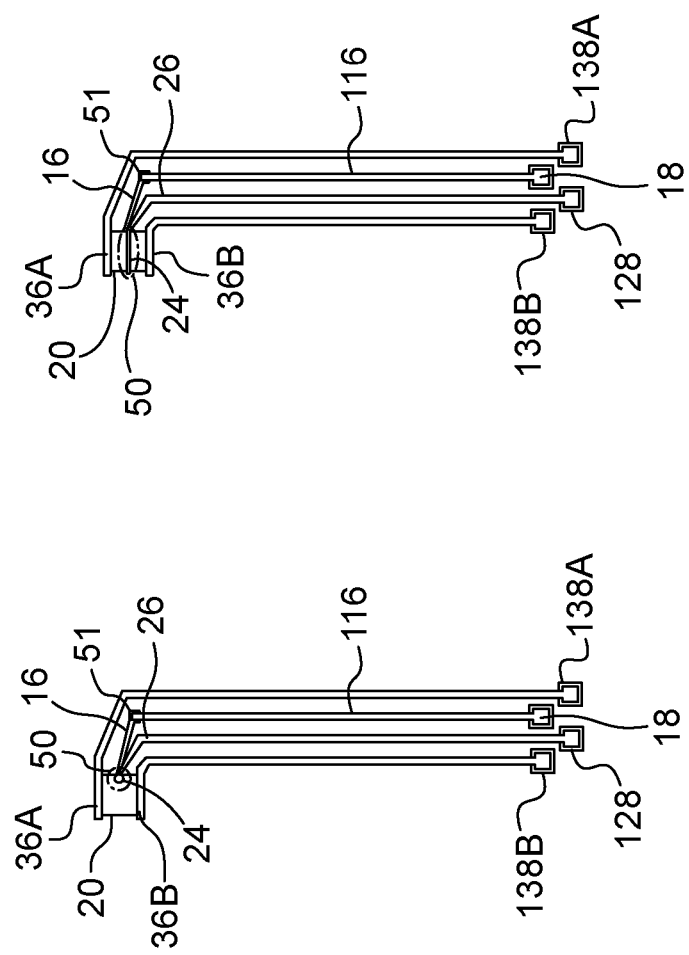

INTEGRATED TEMPERATURE CONTROL WITHIN A DIAGNOSTIC TEST SENSOR

FIELD

The invention relates to a test sensor, such as a diagnostic test sensor or strip, a heater and thermocouple device for use in a test sensor and in other assays, and to a method of manufacturing such a test sensor or device, and a method of conducting an assay using the test sensor or device.

BACKGROUND

Most diagnostic assays are dependent to some degree on the temperature at which the analysis takes place. Temperature measurement and correction is one approach that is employed to mitigate the effects of temperature on an assay response.

In many portable diagnostic devices using disposable test elements e.g. test sensors such as test strips, the temperature of the assay can be difficult to measure and/or control. Temperature measurement is often done within a measurement instrument and the temperature measured can be quite different to that of the strip itself on which the assay is located.

It would be preferable to be able to control the temperature at which the assay reaction takes place but this requires both temperature measurement at the location where the assay reaction occurs and a means to change the temperature at which the assay takes place in that location.

A typical solution to heating the test area is the provision of a heating block in contact with the test strip. There are a number of drawbacks to this solution in that the thermal mass of the heater block limits the response time to any desired temperature change. Further, it typically requires the test strip to be inserted deep inside an instrument that powers a heater block so that it lies next to the heater block almost in its entirety, adding to the strip size and contamination risk. In addition, the temperature of the heating block is known but assumptions about the thermal transfer to the strip and the assay area need to be made and hold true for all strip insertions. In practice, these assumptions cannot be said to hold true for all strip insertions. Therefore, there may well be a disparity between the assumed and actual temperature of the assay and a disparity in temperature measurement from one strip to the next.

Heating and temperature measurement methods are required that are located as close as possible to where the measurement is taken; have rapid response times; are easily manufacturable using materials and processes commonly used in diagnostic device manufacture and are cheap enough to be applied to affordable single-use disposable test devices.

Nucleic acid tests (NATs) in particular also need either precise temperature cycling (for Polymerase Chain Reaction (PCR) based amplification) or well controlled elevated temperatures (for isothermal amplification methods). A very local, fast responding and accurate means to control the temperature exactly where it is required would use less energy and minimise the effects of raised temperatures beyond where they were needed.

In the case of a printed heater on a diagnostic test device such as a test strip, the voltage applied to the heater element is typically 5-20V (5000-20,000 mV), whereas the voltage output from a thermocouple in the temperature range relevant to diagnostic devices (e.g. from ambient to 100° C.) is typically less than 6 mV and can be less than 1 mV i.e. around 4 orders of magnitude smaller than the voltage across the heater element. Thus the heater element and thermocouple must be physically and electrically isolated from each other, leading to at least five different material lay down steps in order to place the thermocouple and heater element in the same location (or very nearly in the same location). The five different material lay down steps are typically as follows.

|    | Material               | Electrical Conductivity |
|----|------------------------|-------------------------|
| 1. | Heater connector tracks | High                    |
| 2. | Heater element         | Medium                  |
| 3. | Insulating layer       | Negligible              |
| 4. | Thermocouple material 1 | High                    |
| 5. | Thermocouple material 2 | High                    |

Any heater element is preferably provided with a corresponding measurement of the temperature to achieve more reliable control, as the lot to lot variation in materials and changes within a heater element due to the heating mean that the temperature cannot reliably be predicted for a particular applied voltage.

U.S. Pat. No. 4,004,948 SMITH describes painting lines of two dissimilar thermal element materials on a non-conducting substrate intersecting at a location where the temperature is to be measured.

U.S. Pat. No. 4,438,291 EICHELBERGER describes a low-cost thermocouple using a first conductor, an insulating layer and a second conductor.

WO2005/114649 SMITH describes a silk screen printed thermocouple.

U.S. Pat. No. 9,786,829 and WO2011/116303 both to GRANDE describe a thermocouple device comprising a flexible, non-planar substrate, first and second printed thermocouple elements, and medical devices comprising the thermocouple. The thermocouple can be made to function as both a heater and a temperature sensor by use of a switching circuit.

US2009/0325205 (also published as U.S. Pat. No. 8,349,259) FUJII describes a method for using temperature correction in biosensors.

EP1398997 NELSON describes a flexible heater device.

LEE et al describe "Application of Screen Printing in Flexible Miniature Thermocouple Process Development". International Journal of Electrochemical Science 10 (2015) 3082-3087.

OLSEN et al describe "The non-metallic thermocouple: a differential temperature probe for use in microwave fields" in Radio Science, Vol 14, issue 65, November 1979, pages 81-84.

Printed flexible heaters and warming elements are available from GSI Technologies at http://www.gsitech.com/heater-and-warming-element-printing-ptc/

The present invention seeks to alleviate one or more of the above problems or problems in the art.

SUMMARY

In a first aspect of the invention there is provided a test sensor comprising a heater and thermocouple device 100, the heater and thermocouple device 100 comprising: a substrate 10;

on the substrate 10, a first layer 12 of a first conductive material of a first conductivity comprising: a first thermocouple element 14; a first connector track 16 connected to the first thermocouple element 14; a resistive heater element 20; and preferably in which at least part of the first thermocouple element 14 is comprised of a portion of the resistive heater element 20;

a second layer 22 of a second conductive material of a second conductivity comprising: a second thermocouple element 24 in contact with the first thermocouple element 14 (e.g. together with the first thermocouple element 14 forming a thermocouple junction 50); a second connector track 26 connected to the second thermocouple element 24; and two heater connector tracks 36A, 36B spaced apart and connected to respective portions of the resistive heater element 20, each on a respective side of the first and second thermocouple elements 14, 24 e.g. one on a portion of resistive heater element 20 to one side of first and second thermocouple elements 14, 24 and one on a portion of resistive heater element 20 to the other side of first and second thermocouple elements 14, 24.

Typically the test sensor comprises a test area, e.g. a generally 2 dimensional area or a sample chamber or flowpath, for receiving sample and conducting an assay. A flowpath allows sample to flow through it, whereas a sample chamber may simply receive sample (e.g. from a flowpath or otherwise).

Preferably, the second conductivity of the second material is greater, preferably significantly greater, than the first conductivity of the first material. In the case of thin films, sheet resistivity is a useful measure of conductance. Where the first material is a screen printed carbon paste and the second material is a screen printed silver paste then the sheet resistivity of the first material is about 200 ohms (Ω) per square @ 10 μm sheet thickness and the second about 30 milliohms (mΩ) per square @ 10 μm i.e. the second material is at least between 3 to 4 orders of magnitude more conductive than the first material.

When powered, field lines extend between heater connector tracks 36A, 36B creating current flow and Joule resistive heating in heater element 20. The layout of the field lines will depend on the separation, orientation, and layout (e.g. peripheral shape of opposing edges) of each of the heater connector tracks 36A, 36B and the second thermocouple element 24.

Preferably, the resistive heater element 20 and heater connector tracks 36A, 36B are configured to provide a uniform electric field, for example a generally or substantially uniform electric field across at least part of the resistive heater element 20. Preferably a uniform electric field 13 is provided across at least 50%, or at least 80%, or at least 90%, or at least 95%, of the area of resistive heater element 20 When a resistive heater element 20 of uniform geometry is provided comprised of material of substantially homogenous resistivity in a uniform electric field, substantially even resistive heating is more easily provided across the resistive heater element 20. This is especially useful for swift, accurate heating of small sample volumes in a test sensor e.g. of a test area in, or adjacent to, resistive heater element 20. This is also useful for accurate control (feedback) of the temperature of the resistive heater element 20 via the thermocouple 50.

Preferably the second thermocouple element 24 is configured to enable a uniform electric field to be provided, for example a generally or substantially uniform electric field across at least part of the resistive heater element 20.

The second thermocouple element 24 may have a free distal end on resistive heater element 20, which may be a rounded free distal end. The area of overlap with resistive heater element 20 may be rounded e.g. semi-circular.

Preferably, the area of the second thermocouple element 24 on resistive heater element 20 is ≤20%, or ≤10%, or ≤5% of the area of resistive heater element 20 between conductive tracks 36A, 36B.

Preferably the second thermocouple element 24 is configured to enable a uniform electric field, for example a generally or substantially uniform electric field across at least part of the resistive heater element 20 in co-operation with one or both heater connector tracks 36A, 36B.

Preferably, the second thermocouple element 24 has at least one edge parallel to a facing edge of one of the heater connector tracks 36A, 36B.

Preferably, the second thermocouple element 24 has two edges parallel to respective facing edges of heater each connector track 36A, 36B.

Preferably, the heater connecter tracks 36A, 36B have facing edges which are parallel to one another (e.g. their central longitudinal axes are parallel to each other).

Preferably, the heater connecter tracks 36A, 36B are parallel to one another. Preferably these heater connector tracks 36A, 36B are each of constant width along their length.

Preferably, the first and/or second thermocouple elements are parallel to one or both the heater connector tracks 36A, 36B (e.g. their central longitudinal axes are parallel to each other).

Preferably, at least a portion of one or both of the first and second thermocouple element(s) 14 lie(s) along a region of constant temperature within resistive heater element 20.

Preferably, one or both of the first and second thermocouple element(s) 24 lie(s) along a region of equipotential within resistive heater element 20.

Preferably, the first thermocouple element 14 and/or first connector track 16 intersect(s) a periphery 76 of the resistive heater element 20 at a first location and the second thermocouple element 24, and/or second connector track 26, intersect the periphery 76 at a second location, and the first and second locations are at the same temperature and/or at the same potential. The first and second locations may be the same location, or these may be different locations.

Preferably, the first thermocouple element 14, and/or first connector track 16, intersect (meet) the periphery 76 of the resistive heater element 20 at a different location to the location where the second thermocouple element 24, and/or the second connector track 26, intersects the periphery 76.

Preferably, the first thermocouple element 14, and/or first connector track 16, intersect (meet) the periphery 76 of the resistive heater element 20 at a location at the same temperature as that where the second thermocouple element 24, and/or the second connector track 26, intersects the periphery 76. Thus the temperature drop along each respective combined thermocouple element 14, 24 to a 'cold' end of a respective connector track 16, 26 are the same.

Preferably, the first thermocouple element 14, and/or first connector track 16, intersect (meet) the periphery 76 of the resistive heater element 20 at a location at the same potential as that where the second thermocouple element 24, and/or the second connector track 26, intersects the periphery 76. Thus, the potential gradient to each respective connector track 36A, 36B from the thermocouple junction 50 is the same for both thermocouple elements. Indeed, preferably the entire thermocouple junction 50 lies along a region of the same potential so the portions of the resistive heater 20 each side of it are exposed to the same voltage gradient.

Preferably, the thermocouple elements 14, 24 lie substantially in between the heater connector tracks 36A, 36B.

Preferably the thermocouple elements lie entirely in between the heater connector tracks 36A, 36B e.g. so that no portion of one, or preferably both, of the thermocouple elements 14, 24 extend(s) beyond a direct straight line between opposing corresponding ends of heater connector tracks 36A to 36B. Thus, it is preferred that the thermocouple elements 14, 24 lie directly between opposing portions of connector tracks (as in FIG. 2A) but these may be slightly to one side i.e. not lying entirely between connector tracks 36A, 36B, see FIG. 3C and portion A2 in FIGS. 13A and 13B.

Preferably, the first and second thermocouple elements 14, 24 are equidistant from both heater connector tracks 36A, 36B.

Preferably, one or both first and second thermocouple elements 14, 24 and/or one or both heater connector tracks 36A, 36B are elongate, optionally linear, preferably of rectangular shape.

Preferably, at least one, optionally all, of the first thermocouple element 14, the first connector track 16, the second thermocouple element 24, the second connector track 26 and the heater connector tracks 36A, 36B are elongate, preferably substantially rectangular, having a narrow lateral width; in other words these are, preferably, relatively slender structures e.g. compared to resistive heater element 20.

Preferably, the heater connector tracks 36A, 36B are of comparable (preferably the same) size and/or shape as one another.

Preferably, the length of the first and second thermocouple elements 14, 24 are the same or less than that of one, and preferably both, heater connector tracks 36A, 36B.

Preferably, the first and second thermocouple elements 14, 24 are of substantially the same size and shape. Typically the first thermocouple element 14 in the first layer is delimited by the size and shape of the second thermocouple element 24 of the second layer in contact with it. Particularly within the region of the heater resistive element 20, the first and second thermocouple elements will be at essentially the same average temperature since the second thermocouple element 24 conducts heat relatively well.

The first and second connector tracks 16, 26 are preferably contiguous and preferably integrally formed with, respectively, first and second thermocouple elements 14, 24. In at least one embodiment, a portion of thermocouple junction 50 (overlapping first and second thermocouple elements 14, 24) is formed from a portion of the first layer lying outside the periphery 76 of the heater resistive element forming part of the first thermocouple element 14 and overlapping with a portion of the second layer forming part of the second thermocouple element 24 also lying outside the periphery 76 of the heater resistive element. Preferably, the area of overlap beyond the periphery 76 of heater 20 of the first and second layers to form part of first and second thermocouple elements 14, 24 is small, preferably less than 20%, more preferably less than 10%, more preferably less than 5%, of the total area of the thermocouple junction 50 (defined by the overlap between first and second thermocouple element 14, 24). Preferably, the overlap beyond periphery 76 is zero. In this way, preferably, the thermocouple junction 50 lie(s) entirely within a periphery 76 of the heater element 20, although it may intersect (meet) with the periphery 76.

Beyond the periphery 76 of the resistive heater element 20, the temperature will drop off, but the area of overlap of the first and second thermocouple elements 14, 24 beyond the periphery 76 is preferably small. In any case, the temperature of each of the first and second thermocouple elements 14, 24 beyond the periphery 76 will be closely related to each other and will likely be substantially the same because of the conductivity of the second layer.

Preferably, the resistive heater element 20 has a periphery 76, and the periphery 76 has at least four edges (and preferably only four edges) and the heater connector tracks 36A, 36B extend along two opposing edges of the periphery 76 (preferably along the entirety of one or both opposing edges) so that most, preferably substantially all, of the resistive heater element 20 is heated between the heater connector tracks 36A, 36B.

It will be understood that the second layer 22 may have a continuous portion but is generally discontinuous having second thermocouple element 24 separate and distinct from the two spaced apart heater connector tracks 36A, 36B.

The resistive heater element may be any suitable shape e.g. generally or substantially circular, elliptical, rectangular, rhomboid, square, diamond, polygonal. It may be elongate but preferably its longest dimension is no more than double its widest dimension. Preferably it is four sided, with preferably two pairs of parallel edges.

Preferably, opposing edges of resistive element 20 are of the same length and/or the corners of the resistive heater element 20 are each 90° (substantially 90°).

Preferably, one or more of the resistive heater element 20, the first thermocouple element 14, and the second thermocouple element 24 are configured so that the voltage indicative of temperature remains substantially unaffected by the voltage applied to the resistive heater element. There are various geometries and/or arrangements that can assist with this, as is apparent from the geometries and arrangements described in this disclosure.

Preferably, the geometry of the layers is arranged so that the field developed across the resistive heater element 20 is parallel to (e.g. generally or substantially parallel) to the uppermost surface of the first thermocouple element 14 (and so to the interface between the first and second thermocouple elements 14, 24 when these are in direct contact with one another). Preferably, the geometry is configured to provide a 'vertical' thermocouple junction 50 across 'horizontal' lowermost and uppermost surfaces of the thermocouple elements 14, 24 respectively. There will be other configurations (physical arrangements) that could be envisaged from the teaching in this application that could be used to provide electric field parallel to the uppermost surface of the first thermocouple element 14 in further embodiments of the invention as would be understood by those skilled in the art.

Preferably, the thermocouple junction 50 (the area of contact between the two thermocouple elements 14, 24) lies in a substantially horizontal plane (with respect to substrate 10). The electric field within any horizontal plane is preferably substantially uniform. The presence of a second thermocouple element of greater conductivity than the first (and in contact with it) provides a region of equipotential along the thermocouple elements 14, 24 in a lateral (horizontal) direction. Preferably, in addition, the thermocouple element 24 is provided along a region of equipotential between heater connector tracks 36A, 36B. The expected thermocouple voltage is a few mV. Any voltage indicative of temperature at the 'cold' ends of contact tracks 16, 36 e.g. at contact pads 18, 38 due to the voltage applied to the resistive heater element (in a lateral or horizontal direction) resulting in Joule heating is preferably negligible i.e. <<mV.

To explain further, preferably the first and second thermocouple elements (e.g. forming thermocouple junction 50)

lie along a line of equal temperature and/or equipotential between connector tracks 36A, 36B. As the second thermocouple element 24 is (relatively) highly conductive, it will also provide, in itself, a region of equal temperature and equipotential. By arranging for this relatively conductive second thermocouple element 24 to lie along a region of equipotential in the resistive heater element 20 between connector tracks 36A, 36B, more even heating can be achieved. Thus, preferably, each respective thermocouple element 14, 24 are at the same 'hot' temperature and their respective connector tracks 16, 26 will experience the same temperature gradient to their respective 'cold' or 'reference' end(s) at contact pads 18, 28.

Second thermocouple element 24 may be located wholly, or at least partly, anywhere on (or under) resistive heater element 20 but is preferably centrally located, preferably equidistant from each substantially parallel of heater connector tracks 36A, 36B. In this way, in the presence of a uniform electric field between connector tracks 36A, 36B and a uniform resistive heater element, regions of the resistive heater element 20 lying between each respective track 36A, 36B and the second thermocouple element 24 will be of similar resistance (indeed of similar resistance between corresponding points on the heater connector tracks 36A, 36B and thermocouple element 24).

Preferably, the second layer overlays the first layer.

Preferably at least one, optionally all, of the first thermocouple element 14, the first connective track 16, the resistive heater element 20, the second thermocouple element 24, the second connector track 26, the heater connector tracks 36A, 36B are (e.g. generally or substantially) planar e.g. two-dimensional having two lateral dimensions substantially greater than a respective thickness (or depth) on substrate 10.

Preferably, the first layer 12 comprises a first contact pad 18 connected to the first connector track 16.

Preferably, the second layer 22 comprises a second contact pad 28, 128A connected to the second connector track 26.

Preferably, the first layer 12 comprises a second contact pad 128 connected to the second connector track 26.

It will be apparent to those skilled in the art that any additional junctions between the first and second materials, or indeed other materials remote from the heater element 20, will not affect the voltage developed indicative of temperature due to the thermal gradients from the 'hot' to the 'cold' ends of thermocouple elements 14, 24 and connector tracks 16, 26 because, in this in vitro design, these will all be at the same temperature as the 'cold' or 'reference' ends.

Preferably, the first thermocouple element 14, resistive heater element 20, first connector track 16, and optionally the first contact pad 18 connected to the first connector track 16, form a continuous portion of the first layer 12.

Preferably, the second thermocouple element 24, second connector track 26, and optionally the second contact pad 28, 128A connected to the second connector track 26, form a continuous portion of the second layer 22.

Preferably the thermocouple elements 14, 24 are spaced from the peripheral edges of the resistive heater element 20 (preferably equispaced from two respective opposing portions of the periphery e.g. two opposing edges on which the heater connector tracks 36A, 36B are overlaid).

Preferably, one of both thermocouple elements 14, 24 extend across the resistive heater element 20 from one portion of the periphery 76 of resistive heater element 20 to an opposing portion of the periphery 76.

Preferably, the distal or terminal ends of one or both of the thermocouple elements 14, 24 meet the periphery 76, but one or both of these may stop short by a small amount, or may extend beyond the periphery by a small amount. Any such non-overlapping extension beyond the periphery is immaterial.

Preferably the first and second thermocouple elements 14, 24 do not overlap one another or overlap to a small, preferably a minimal, extent beyond the periphery 76 of the resistive heater element 20.

Preferably, the first connector track 16 intersects (meets) the periphery 76 of the resistive heater element 20 on an opposing portion, preferably a directly opposing portion of the periphery 76, to that where the second connector track 26 intersects the periphery 76.

Preferably, the overlap of the first and second thermocouple elements 14, 24 lies, substantially, preferably entirely, within the periphery 76 of the resistive heater element 20.

Preferably the overlap of the first and second thermocouple elements 14, 24, i.e. area of the thermocouple junction 50, that lies outside the periphery 76 of the resistive heater element 20 is small, and preferably is negligible.

Preferably, the first material is selected from one or more of a semi-conductive material, carbon, bismuth, constantan, silicon, germanium, antimony, iron, nichrome (e.g. nickel and chromium (optionally iron) alloys), and molybdenum; and/or the second material is selected from any one or more of a metal, silver, copper, gold, aluminium and nickel.

Preferably, the first and second materials have a relative Seebeck coefficient of 5-65 µV/K, or 10-50 µV/K, or 10-25 µV/K, or 15 to 20 µV/K or 17 µV/K.

Preferably, the resistive heater element 20 defines a heated test area.

Preferably, the test sensor comprises a sample chamber, and/or flowpath, for receiving sample.

Preferably, the first and second thermocouple elements 14, 24 and the resistive heater element 20 are located adjacent to or within the sample chamber, and/or adjacent to or within the flowpath.

The sample chamber may be provided by a flow path e.g. a capillary flow path, or may be filled by capillary flow into it. Alternatively, in addition, the sample chamber may have an open side wall or roof portion to facilitate introduction of a sample e.g. under gravity.

In a second aspect of the invention there is provided a heater and thermocouple device 100, the heater and thermocouple device 100 comprising: a substrate 10;

on the substrate 10, a first layer 12 of a first conductive material of a first conductivity comprising:
　a first thermocouple element 14;
　a first connector track 16 connected to the first thermocouple element 14;
　a resistive heater element 20;
　and in which at least part of the first thermocouple element 14 is comprised of a portion of the resistive heater element 20;

a second layer 22 of a second conductive material of a second conductivity comprising:
　a second thermocouple element 24 in contact with the first thermocouple element 14 (e.g. together with the first thermocouple element 14 forming a thermocouple junction 50);
　a second connector track 26 connected to the second thermocouple element 24; and two heater connector tracks 36A, 36B spaced apart and connected to respective portions of the resistive heater element 20, each on a respective side of the thermocouple elements 14, 24.

In a third aspect of the invention there is provided a method of manufacturing a test sensor or a thermocouple or a device as described herein comprising:

providing a substrate 10;

providing on the substrate 10 (e.g. by wet or dry deposition such as painting, screen printing) a first layer 12 of a first conductive material of a first conductivity comprising:
a first thermocouple element 14;
a first connector track 16 connected to the first thermocouple element 14;
a resistive heater element 20 in which at least part of the first thermocouple element 14 is comprised of a portion of the resistive heater element;
and
providing on the substrate 10 a second layer 22 of a second conductive material of a second conductivity comprising:
a second thermocouple element 24 in contact with a portion of the first layer to form the first thermocouple element 14 (e.g. together with the first thermocouple element forming a thermocouple junction 50);
a second connector track 26 connected to the second thermocouple element 24;
two heater connector tracks 36A, 36B spaced apart and connected to respective portions of the resistive heater element 20, each on a respective side of first and second thermocouple elements 14, 24.

Preferably, the first layer is laid down on the substrate before the second layer.

In a fourth aspect of the invention there is provided a method of conducting an assay comprising: providing a test sensor, or heater and thermocouple device, as described herein with a sample chamber and/or flow path; introducing a sample into a sample chamber and/or flowpath; heating the sample using the heater and thermocouple device; making a measurement on the sample; optionally, allowing the sample to cool and repeating the measurement; optionally, holding the sample at a predetermined temperature and repeating the measurement.

In one embodiment the invention concerns a thermocouple controlled heating element within a disposable test strip using (preferably only using) materials commonly used in biosensor manufacture and with a reduced, preferably a minimum, number of material deposition steps. Preferably, the heating element and thermocouple junction are both constructed from the same materials.

Several embodiments of the invention are described and any one or more features of any one or more embodiments may be used in any one or more aspects of the invention as described above.

BRIEF DESCRIPTION OF THE DRAWINGS

The present invention will now be described, by way of example only, with reference to the following figures. In this document, like reference numerals refer to like features and reference numerals are used for the purpose of illustration and are not considered to be limiting.

FIG. 3A shows a plan view of a heater and thermocouple device for use as a test sensor with a first layer of a first conductive material, the first layer here having continuous (14, 16, 18, 20) and discontinuous portions (128, 138A, 138B, and 14, 16, 18, 20 together as a continuous portion discontinuous from the remainder of the first layer).

FIG. 3B shows a plan view of a second layer of a second conductive material for use in the device of FIG. 3A, the second layer here having three discontinuous portions (24 and 26, 36A and 136A, 36B and 136B).

FIG. 3C shows a plan view of the heater and thermocouple device 100 including the first and second layers of FIGS. 3A and 3B with the second layer superimposed on the first layer to form a thermocouple junction 50 (comprising first and second thermocouple elements 14, 24) and a heater 60 (comprising a resistive heating element 20 and spaced apart heater connector elements 36A, 36B) together forming an integrated heater and thermocouple device 100 for use in a test sensor.

FIG. 8 shows a plot of temperature against time showing the calibrated output temperature from a printed thermocouple when an associated heater in a prototype integrated heater and thermocouple device is switched on.

FIGS. 16A and 16B show respective plan views of integrated heater and thermocouple devices in further alternative embodiments according to the invention, here seen from below, as if through a transparent substrate, indeed a transparent substrate may be used.

FIG. 17 shows a photographic plan view of an actual device such as that seen in FIG. 16A or 16B (here with the right hand heater connector track 136A omitted).

DETAILED DESCRIPTION

It will be understood by those skilled in the art that any material properties, temperatures, potentials, electric fields, dimensions, shapes etc. and directions (such as height, depth, width, lateral, planar, horizontal etc) are to be understood as lying within the usages, tolerances and limits for devices used in assays and diagnostics, such as test sensors and test strips, and these terms should be interpreted with this in mind. Further, the term test strip is used as an example of a test sensor on which a fluid, typically liquid, sample is tested. This term is not intended to be limiting and there are various forms, sizes and shapes of test sensors with which the invention may be used and the test strip (a relatively rigid, generally planar test device of any size or shape) is one particularly preferable example.

The heater and thermocouple device 100 of the invention is an integrated device providing two functions of heating and control. It is particularly useful when formed including a substrate, and in which the substrate is typically generally or substantially planar and may form the main substrate of a test sensor such as a test strip.

Figure 1A:
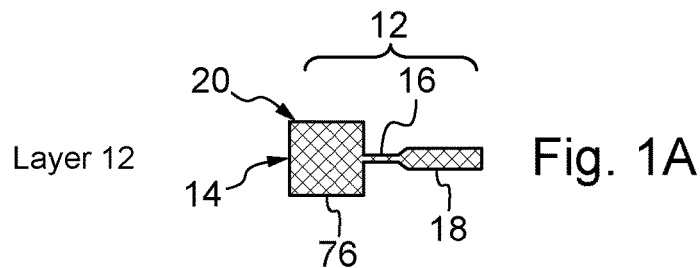
FIG. 1A shows a plan view of a first layer of a first conductive material.

In FIG. 1A, a first layer 12 of a first conductive material is laid down on a substrate 10 (not shown). The first layer 12 comprises a first thermocouple element 14, a first connector track 16, a first contact pad 18 and a resistive heating element 20. The four components (here in this example) form a continuous portion of first layer 12. Layer 12 may have additional portions e.g. additional continuous (and/or indeed discontinuous) portions similar, or the same, as those shown in FIG. 1A (not shown) or indeed different separate portions (not shown). Thus, multiple heater and thermocouple devices of the invention may be formed in one pair of first and second layers 12, 22.

The first layer 12 (and/or the second layer 22 described below) may be provided in the form of a dry film, having, prior to construction, two opposed, generally parallel planar surfaces. Alternatively, one or both may be formed by wet deposition techniques (e.g. screen printing) forming, when dry, two generally parallel planar surfaces one of which is exposed, the other of which is concealed in contact with the surface on which it is deposited.

Resistive heater element 20 is shown here as a four-sided shape (here a square) having two pairs of opposing parallel sides of the same length forming its periphery 76. Resistive heater element 20 may be of any suitable size and shape but is preferably generally or substantially planar as determined by the uppermost exposed surface of substrate 10 on which it is deposited, and its deposition method (e.g. wet or dry deposition). The resistivity of the resistive heater element will be determined both by the conductivity of the first material and its shape and size (height, width, depth etc.). Here, preferably the first material is of relatively high resistivity (compared to the second material—see below) and preferably it is of (e.g. generally or substantially) homogenous resistivity to facilitate more uniform heating. The first thermocouple element 14 forms part of resistive heater element 20, here a rectangular portion of heater element 20 spanning from one side of square-shaped periphery 76 to an opposite side but not as yet defined as such at this stage of manufacture (although it may be).

Figure 1B:
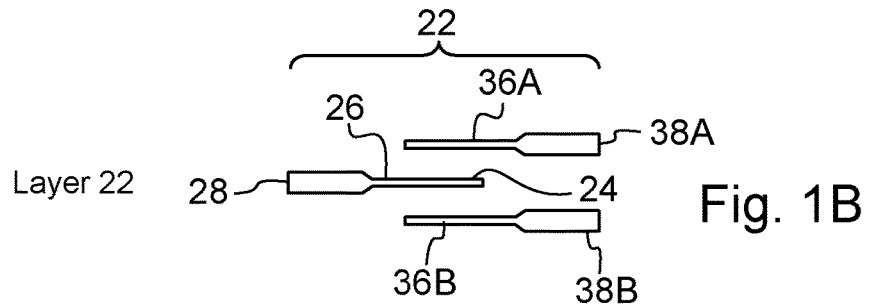
FIG. 1B shows a plan view of a second layer of a second conductive material.

In FIG. 1B, a second layer 22 comprising three separate portions of a second conductive material of a second conductivity have been laid down. Preferably, the second layer 22 is laid over the first layer 12 but the first layer 12 may be laid over the second layer 22 to similar effect and to provide the same function(s). Preferably, these contact each other directly in the region of overlap forming a direct interface. The second layer 22 comprises a second thermocouple element 24 of narrow, rectangular shape (seen in plan view) of constant width (in this example) connected to a first connector track 26 which in turn connects to and terminates in a second contact pad 28. The second layer 22 also comprises spaced apart heater connector tracks 36A and 36B spaced, sized and shaped to overlap the opposite edges of the periphery 76 of resistor heater element 20 providing one connector track 36A, 36B to each side of the first and second thermocouple elements 14, 24. Heater connector tracks 36A and 36B are also here of narrow, rectangular shape, being elongate and of constant width (in this example). These connect to and terminate in connector pads 38A and 38B typically of wider width. Second layer 22 comprises a second material of a second conductivity which is, compared to the conductivity of the first material of first layer 12, relatively high. The heater connector tracks 36A, 36B may be in direct or indirect contact with resistive heater element 20.

Thus, both materials have charge mobility carriers and may be of conductive or semi-conductive materials. Nevertheless, the first and second materials are selected so that the two materials have differing Seebeck coefficients. It is easier to talk about relative Seebeck coefficients between two materials than absolute values for a particular material. The relative Seebeck coefficients of known materials include those for Chromel-Constantan, Chromel-Alumel. For standard thermocouple types the relative Seebeck coefficients range from 60 µV/K for Type E thermocouple (Chromel-Constantan) to 8 µV/K for a Type B (Platinum(30% Rhodium)-Platinum(6% Rhodium)). The most common thermocouple is probably Type K (Chromel-Alumel) with a relative Seebeck coefficient of 40 µV/K. In our example the relative Seebeck coefficient can be determined from FIG. 5 to be about 17 µV/K.

Materials that could be used include any one or more materials such as carbon, bismuth, constantan, silicon, germanium, antimony, iron, nichrome, molybdenum etc. for the first material including the heater element, while any one or more materials such as metals including silver, copper, gold, aluminium and nickel etc. may be used for the second material for the highly conductive tracks 36A, 36B, 136A, 136B. Other materials and material combinations will be apparent from this disclosure.

Figure 2A:
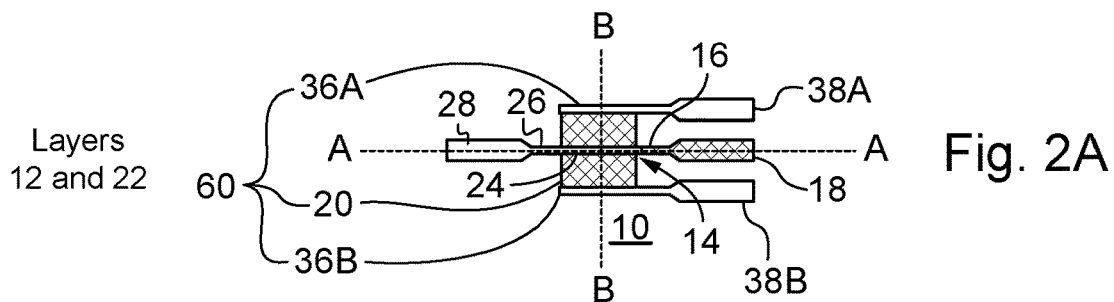
FIG. 2A shows a plan view of the first and second layers of FIGS. 1A and 1B with the second layer superimposed on the first layer to form an integrated heater and thermocouple for use in a test sensor.
Figure 2B:
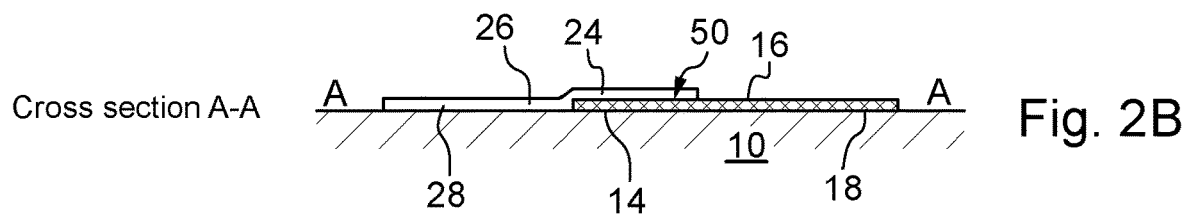
FIG. 2B shows a side cross-sectional view of FIG. 2A along AA illustrating thermocouple junction 50.
Figure 2C:
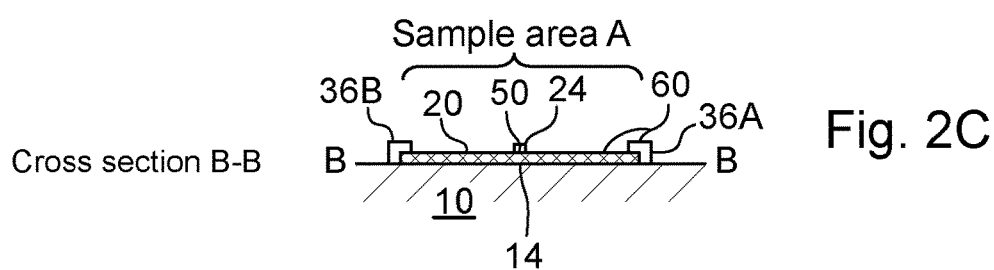
FIG. 2C shows a side cross-sectional view of FIG. 2A along line B-B orthogonal to A-A illustrating heater 60.

In FIGS. 2A to 2C, second layer 22 is shown overlaying first layer 12. It can now be seen that second thermocouple element 24 overlaps a central portion of resistive heater element 20 between the connector tracks 36A, 36B and is here of rectangular shape. Thus, the second thermocouple element 24 defines that portion of the first layer 12 and typically the resistive heater element 20 that will form and function as first thermocouple element 14. First and second thermocouple elements 14, 24 overlap and are, preferably directly, in contact with one another and are of the same size and shape, here rectangular and further elongate, parallel to and centrally located in between heater connector tracks 36A, 36B. Respective opposing edges of each of heater connector tracks 36A, 36B and of second thermocouple element 24 are preferably parallel to one another so that field lines extend perpendicularly and evenly between these to provide a uniform electric field. Preferably the field lines on both sides of the second thermocouple element 24 are parallel to one another.

A thermocouple junction 50 (best seen in FIG. 2B) is formed at the interface where the lowermost face of second thermocouple element 24 contacts the uppermost surface of a portion (here the first thermocouple element 14) of resistive heater element 20. Thus, first thermocouple element 14 consists of a portion of resistive heater element 24 in contact with second thermocouple element 24 forming thermocouple junction 50.

The first and second thermocouple elements are preferably in direct contact with one another to form a first, e.g. a 'hot', junction of a thermocouple so that these are at the same temperature as each other. In any thermocouple arrangement there is a reliance on knowing the temperature of the 'cold' or 'reference' junction to determine the difference with, and hence the temperature of, the first 'measuring', or 'hot', junction. The second e.g. 'cold' or 'reference' junction is typically located in the control instrument (e.g. a metering device) remote from any heat source. A calibrating temperature gauge in the control instrument may be provided. Preferably, the temperature of the control instrument, and so of the 'cold' or 'reference' junction, is substantially constant over the time period of the measurement. Indeed, preferably the temperature of the 'hot' or 'measuring' junction is substantially constant over the period of the measurement. Nevertheless it will be understood that the temperature may change from one measurement to the next. Indeed, this 'cold' junction may, in an example embodiment be located on the same substrate but remote from the 'hot' junction.

Heater connector tracks 36A and 36B connect opposing edges of the periphery 76 of resistive heater element 20 to contact pads 38A and 38B so that power can be delivered across resistive heater element 20 in the region between connector tracks 36A and 36B. Thus resistive heater element 20 and connector tracks 36A and 36B form a heater 60 which can be heated by resistive Joule heating, as is well understood.

As the conductivity of the second material is relatively high, the voltage along each respective connector track 36A, 36B will be a respective constant (but different) value along its length. Thus, upon powering, field lines extend between parallel connector tracks 36A and 36B and a uniform electric field is formed across resistive heater element 20 which heats by Joule heating. However, the second thermocouple element 24 extending across resistive heater element 20 is also formed from the relatively highly conductive second material. Therefore, second thermocouple element 24 also represents a region of equipotential. Furthermore, preferably second thermocouple element 24 lies along a region of expected equal temperature, and preferably also equipotential (due to geometries and layout arrangements selected) between heater connector tracks 36A, 36B.

In the region of the second thermocouple element 24, there will be low or minimal Joule heating within the portion of resistive heater element 20 forming first thermocouple element 14, as current will preferentially pass via the higher conductive material of second thermocouple element 24. It is for this reason that it is preferred that second thermocouple element 24 is relatively narrow (e.g. 1 mm or 0.5 mm, 0.25 mm or less in width) to limit the reduction in heating within resistive heater element 20 in the region of first thermocouple element 14 and ensure this 'unheated' region is small and heated quickly by conduction and radiation from neighbouring regions on heater element 20. It is also for this region that second thermocouple element 24 is also preferably located along a centreline of the resistive heater element 20 between connector tracks 36A, 36B so that the current path across the resistive heater element 20 is not foreshortened via the second thermocouple element 24 (e.g. if it were at an angle to the centreline). If it were at such an angle this would result in a region of the resistive heater element being bypassed by the current and so not heated.

Furthermore, by arranging second thermocouple element 24 between and parallel to both first and second conductor tracks 36A, 36B, the field lines are (relatively) unperturbed and extend evenly (and typically perpendicularly) from first conductor track 36A to second thermocouple element 24, and from second thermocouple element 24 to second heater connector track 36B. Indeed, the first and second thermocouple elements 14, 24, and in particular the second thermocouple element 24, has two long edges that are opposite to and substantially parallel to facing edges of connector tracks 36A, 36B facilitating the formation of uniform electric fields between these opposing parallel edges. Where the second thermocouple element 24 has two parallel edges (as it does here being a rectangle) and the connector tracks 36A, 36B are mirror images of one another, and with preferably facing edges parallel to the edges of the second thermocouple element 24, then the field lines from one connector track 36A to the second thermocouple element 24 will be parallel to the field lines from second thermocouple element 24 to the other connector track 36B (except near any free distal end of second thermocouple element 24 e.g. that terminates short of the periphery 76, e.g. see FIG. 3C).

Cross-sections AA and BB respectively are shown in FIGS. 2B and 2C illustrating the placement of first layer 12 on a substrate 10 and subsequently second layer 22 on substrate 10 and first layer 12. The thermocouple junction 50 formed at the interface where first and second thermocouple elements 14 and 24 meet is shown. It will be understood that sample to be heated may be applied, optionally after the application of an additional layer e.g. a waterproof layer, onto the area of resistive heater element 20 which is heated in between connector tracks 36A and 36B. It can be seen, in this example embodiment, that connector tracks 36A and 36B are of similar size, shape and orientation to second thermocouple element 24. It can also be seen that second thermocouple element 24 is positioned centrally in between tracks 36A and 36B and is here equidistant from each along its length. Furthermore it is preferably of the same length (as seen in FIG. 2A). These arrangement(s) assist in providing that the electric field is perturbed as little as possible by the presence of an intervening conductive member in the form of second thermocouple element 24 and (e.g. generally or substantially) uniform heating across (e.g. generally or substantially) the entire resistive heater element 20 is provided. Further, the temperature of the first and second thermocouple elements 14, 24 will be (e.g. generally or substantially) the same along the length of the thermocouple junction 50.

It is of note, particularly in FIG. 2C, that the relative width of first and second thermocouple elements 24 is relatively narrow, e.g. 5 to 10 times narrower, compared to the overall separation of connector tracks 36A and 36B.

It can be seen from FIGS. 1A and 1B and 2A to 2C that, if a specific geometry of components is used, combined with appropriate material selection, the number of different materials and lay down steps can be reduced from five to two, namely step 1—laying down the resistive heater element 20 including a first thermocouple element 14 in a first layer, and step 2—laying down heater connector tracks 36A and 36B and a second thermocouple element 24. Typically step 1 will take place before step 2, but this is not essential, as the second layer may be formed first and over laid with the first layer.

In FIGS. 1A to 2C, in one practical embodiment, the connector tracks 36A, 36B are elongate and parallel to one another and the first (and second) thermocouple elements 14, 24 are elongate and parallel to both the connector tracks 36A, 36B. Preferably these are half way between connector tracks 36A, 36B. The proximal and distal ends of the second thermocouple element 24 meets the periphery 76 at two opposing locations (see FIG. 2A) and the same is true for the underlying first thermocouple element 14. The first and second connector tracks 16, 36 each meet the periphery 76 at an opposite location to each other. Indeed, in FIG. 2A first connector track 16 does not quite meet the periphery 76, as it begins where second thermocouple element 24 terminates but it would be preferable if it did. Such overlaps and slight variations in design details and layout arrangements may depend on the tolerances of the deposition methods selected.

It can also be seen from FIGS. 1A to 2C that the thermocouple junction 50 is preferably formed in such a way that any voltage change across the thermocouple junction 50 due to the voltage applied to the heater element 20 via connector tracks 36A, 36B is very small indeed, preferably close to zero and more preferably zero (volts). This embodiment of the present invention achieves this by both sides (first and second thermocouple elements 14, 24) of the thermocouple junction 50 and in particular second thermocouple element 24 being at the same point (or almost the same point) within the resistive heater element 20. In other words, first thermocouple element 14, defined by the later addition of second thermocouple element 24, preferably follows a line of expected constant temperature and/or preferably also follows a line of expected equipotential in the resistive heater element 20 between first and second connector tracks 36A, 36B. Indeed, the first and second thermocouple elements are placed directly on top of each other as shown in FIG. 2A. Furthermore, preferably the second thermocouple element 24 is located along a line of symmetry in the geometry of the resistive heater element 20 and tracks 36A, 36B so that the voltage (field lines immediately adjacent to thermocouple element 24 are the same or substantially the same along each respective edge (of the second thermocouple element 24 facing tracks 36A, 36B) so no voltage gradient is formed along second thermocouple element 24.

The geometry of the invention, for example the first thermocouple element 14 and, indeed, the second thermocouple element 24, lying along a line of equipotential and/or temperature (or rather along a region symmetrically either side of a line of equipotential and/or temperature) on heater element 20, assists in ensuring that voltage difference developed along the thermal gradients from the 'hot' to the 'cold' junctions measured across contact pads 18 and 28 is independent of the voltage applied across contact pads 38A and 38B. Indeed, the 'ends' of the thermocouple junction 50 typically preferably meet the periphery 76 at the same location or at two locations that are at the same potential and/or at the same temperature (e.g. on opposing parts of the periphery). Various arrangements and geometries can be used, as would be apparent to those skilled in the art from this disclosure.

The voltage generated at the remote ('cold' or 'reference') ends of each connector track 16, 26 is dependent on the thermal gradient from each heated thermocouple element 14, 24 to the unheated remote ends of each respective unheated ('cold') connector track 16, 26. Absent other voltage inputs, the difference in the voltage generated at each remote end of the connector track 16, 26 will depend on the Seebeck effect of the first and second materials and the thermal gradient along each from hot to cold.

To achieve more accurate measurements the two first ends (first and second thermocouple elements 14, 24) need to be at the same temperature and a thermocouple junction 50 at which these overlap and contact one another is a good way of achieving this, as well as providing a measurement circuit.

On resistive heater element 20, the first and second thermocouple elements 14, 24, are preferably evenly heated i.e. there is no voltage developed due to the Seebeck effect along either element. Once these start to cool, i.e. once the thermocouple elements 14,24 or tracks 16, 26, as appropriate, leave the heater 20 and for a while beyond it, there is a thermal gradient (two in fact, one in each of the first and second thermocouple elements and respective conductive tracks). Each element and track develops a voltage gradient (EMF) along this thermal gradient, which in effect produces a voltage difference at their second remote e.g. 'cold' ends.

It can be seen that the invention does not depend on the order of lay down of the two materials or the particular process used to lay down the materials.

The invention allows assays to be done at optimum and controlled temperatures at both ambient and under possibly changing conditions. It also provides the means to have multiple assay areas on the same strip with different temperature profiles if required. The invention is amenable to printing on paper as some recent low cost NATs and is consistent with need for low cost.

Referring now to FIGS. 3A, 3B and 3C, a test sensor comprising a suitable substrate, such as a generally or substantially planar substrate of a suitable stiff material, is shown in plan view suitable substrate materials include polyester, polycarbonate, nylon, polyethylene-naphthalate, polyimide, polyvinyl chloride, polyethylene terephthalate, polypropylene, polystyrene, ceramic, glass, FR-4 board, paper, silicon. A typical strip width is 10 mm and length is 40 mm. A first layer 12 of carbon has been laid down on the substrate by a wet deposit technique, here screen printing, using carbon ink. First layer 12 comprises a rectangular resistive heater element 20, a first thermocouple element 14 comprising both a portion of resistor heater element 20 and a portion of conductive track extending beyond the periphery 76 of heater element 20, a connector track 16 connected to (here contiguous with) the first thermocouple element 14 and terminating in a contact pad 18, and additional separate contact pads 138A, 138B and 128. In FIG. 3B, during a second step, a silver layer 22 has been printed, again here using screen printing and silver ink (as known in the art), comprising heater connector tracks 36A and 36B, heater connector track extensions 136A and 136B, a second thermocouple element 24 and a second connector track 26. An optional contact pad 128A of silver may also be provided in second layer 22. Alternatively, as shown in FIGS. 3A and 3C, a contact pad comprising material of the first layer may be used, as any such resulting additional 'junctions' being at the same temperature as the cold junction contribute nothing to the measured voltage across contact pads 18, 28.

As can be seen in FIG. 3C, the resistive heater element 20 between heater connector tracks 36A and 36B provides a well-defined heated sample area A for receiving sample that can be uniformly heated and accurately heated to a desired temperature. The heated sample area A may be substantially two-dimensional but more usually is delimited by walls of a sample chamber or flowpath (see side walls of spacer layer 80 in FIGS. 10A and 10B). Such a sample flowpath or chamber may be provided with a lid. Preferably it is sized and shaped to be filled by capillary action. The second layer 22 may be laid down first and the first layer may be non-soluble or water proof to facilitate formation of a sample test area A into which liquid sample can be received.

Heater connector track extensions 136A and 136B terminate in carbon contact pads 138A and 138B. Second thermocouple element 24 lies over a portion of resistive heater element 20 and over a portion of a connector track outside the periphery 76 of heater element 20 forming a thermocouple junction 50 that, in this embodiment, spans the periphery 76 of heater element 20. The remaining portions of connector tracks 16 and 26 that do not overlap one another connect first and second thermocouple elements 14, 24 to connector pads 18 and 128 respectively. Conductive second thermocouple element 24 will aid conduction of heat from heater element 20 to first thermocouple element 14.

The resistive heater element 20 reaches different temperatures depending upon the voltage applied as a result of resistive Joule heating. Preferably it is of homogeneous construction, e.g. of homogeneous material laid down in a layer of substantially constant depth, to provide substantially uniform resistive heating across it.

Figure 4:
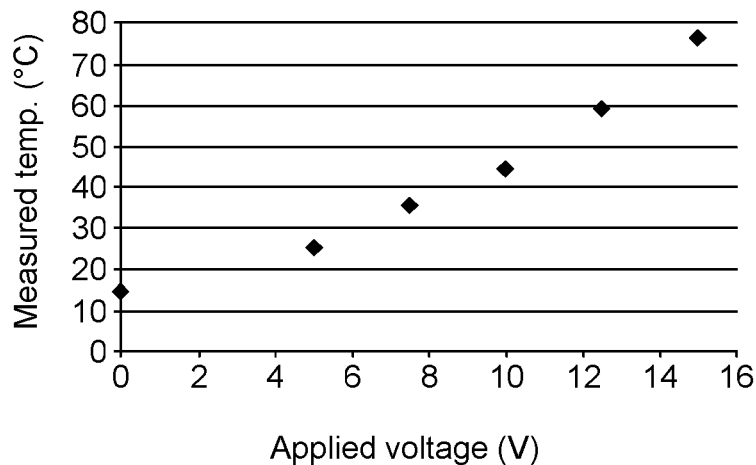
FIG. 4 shows a plot of surface temperature versus applied voltage across the resistive element measured on a prototype device according to one embodiment of the invention.

The temperatures seen in a prototype built according to FIGS. 3A to 3C are a good match with the temperature range required for diagnostic assays including NATs. This is shown in FIG. 4 in which the measured temperature in ° C., as measured by an external temperature gauge, e.g. an off-the-shelf thermometer or thermocouple, is shown against applied voltage in Volts. The surface temperature of the initial device was measured externally. It can be seen that the resistive element 20 behaves well in a linear fashion with respect to applied voltage.

Figure 5:
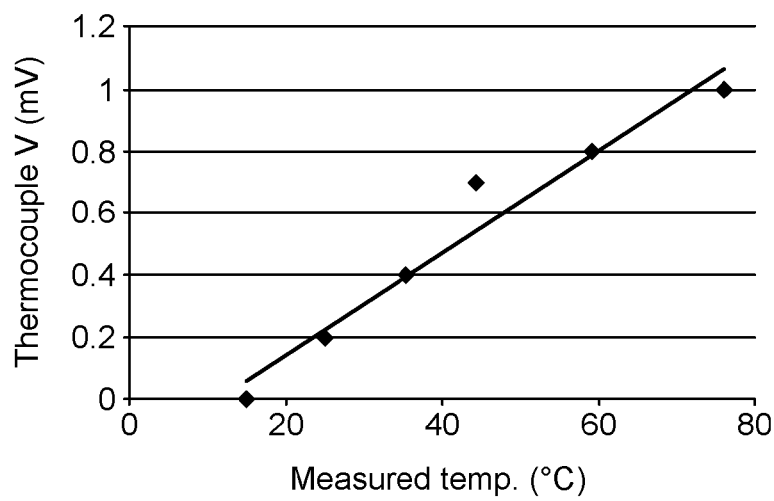
FIG. 5 shows a plot of voltage difference across thermocouple contacts (or more accurately developed by the thermocouple 50 (e.g. with respect to a 'cold' junction)) against (externally) measured temperature of the heater element in a prototype device.

FIG. 5 shows a plot of voltage difference across the thermocouple 50 contact pads 18, 128 (i.e. voltage difference developed along the thermal gradients from the 'hot' to the 'cold' junctions) against the externally measured temperature using the external temperature gauge. It can be seen from FIG. 5 that the temperature-dependent voltage from the thermocouple 50 can also be measured that is unaffected by the voltage across the heater pad. In order to provide the measured temperature shown in FIG. 5, increasing voltages were applied to resistive heater element 20 but nevertheless, there is a linear relationship between the voltage in mV developed across the contact pads 18, 128 (i.e. voltage difference developed along the thermal gradients from the 'hot' to the 'cold' junctions) against temperature. It is quite remarkable that a thermocouple voltage in mV can be measured indicative of temperature at a thermocouple junction 50 touching, and preferably lying on, a resistive heater element across which voltages of units and tens of Volts (a thousand to ten thousand times higher) is present.

Figure 6:
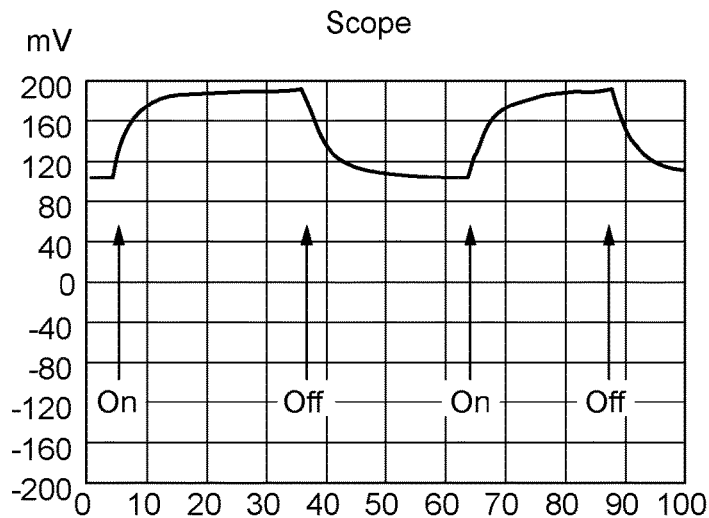
FIG. 6 shows a plot of amplified voltage difference across the thermocouple contacts (or more accurately developed by the thermocouple 50 (e.g. with respect to a cold junction)) during two on/off cycles of the heater 60 in a prototype device.

FIG. 6 shows a plot of amplified voltage difference across the thermocouple contact pads 18, 128 (i.e. voltage difference developed along the thermal gradients from the 'hot' to the 'cold' junctions) during two on/off cycles of the resistive heater element 20 over 100 seconds. It can be seen that, as the heater switches on, the voltage developed across the contact pads 18, 128 as a result of heating 'hot' thermocouple junction 50 increases quickly at first before settling down to a constant temperature. Similarly, upon the switching off of the resistive heater element 20, the voltage drops quickly before settling down to be a smaller constant value.

In a further example, the prototype strip was used with a test rig built using an Arduino microcontroller to determine if a stable on-strip temperature could be provided. An off-the-shelf thermocouple amplifier (MAX 31855) was used to provide an output to the microcontroller which was set to run a proportional integral derivative (PID) control algorithm. The heater was powered using a 9V battery and controlled via one of the microcontrollers' PWM outputs to an optocoupler. The ambient temperature and a number derived from the strip thermocouple output (calibrated to reflect strip temperature) were measured. An off-the-shelf thermocouple was taped to the strip surface and heat sink paste was used to establish a good thermal connection.

Figure 7:
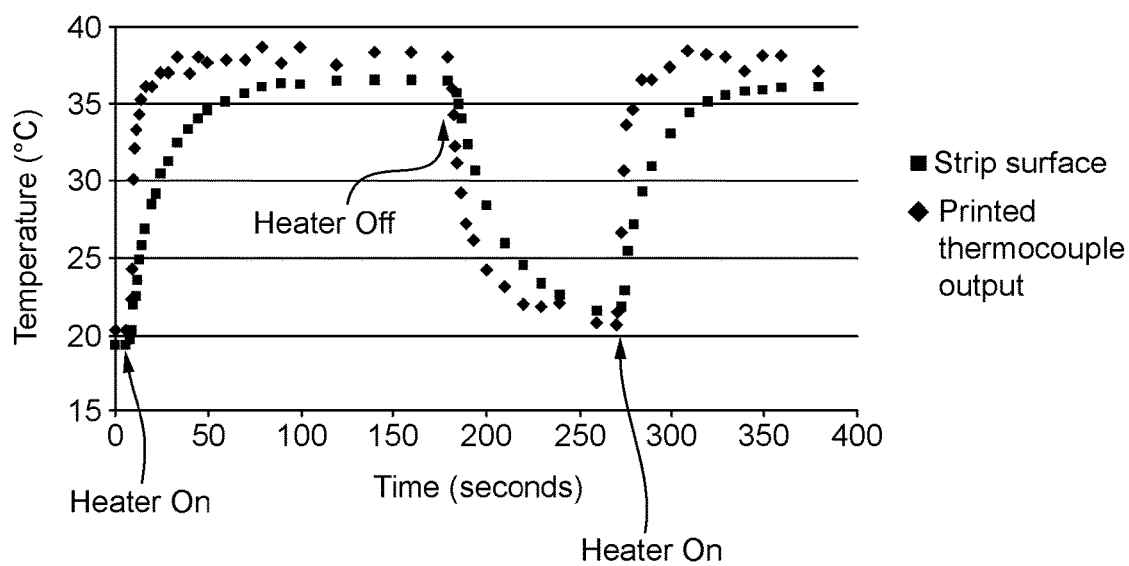
FIG. 7 shows a plot of temperature against time illustrating the externally measured temperature at the strip surface (squares) and the calibrated output temperature from a printed heater and thermocouple device according to the invention showing on a test rig display (diamonds).

FIG. 7 shows a plot of the test rig display (i.e. the desired temperature calibrated to a known temperature) and the measured strip surface temperature measured by an external temperature gauge, here an off-the-shelf thermocouple, over time. The squares show the externally measured strip surface temperature. The diamonds show the printed thermocouple output. It can be seen that the printed thermocouple output matches the externally measured strip surface temperature well.

Figure 8:
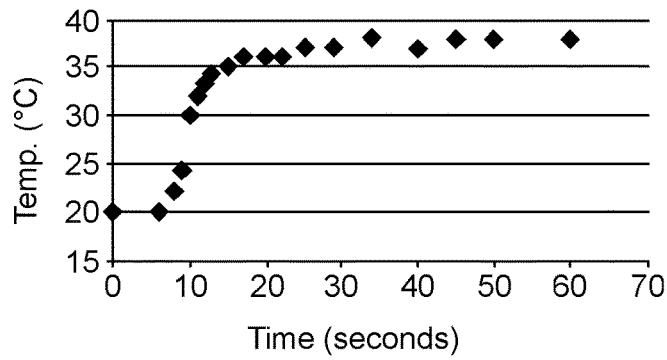

FIG. 8 shows the initial response of the printed thermocouple output against time. It can be seen that the time for the strip to heat up is about 10 s from ambient temperature to just under 40°. It has to be remembered that the sample area being heated is physically very well-defined as being the area of the resistive heater element 20. Now the temperature of the sample area can also be very well controlled and measured at the same time. This on-board strip measurement/control is a big advantage over controlling a remote heat element and assuming good heat transfer or applying voltage to a printed element and hoping it provides the same heating effect each time. The size of the resistive heater element 20 shown in FIGS. 3A to 3C is quite large but this can be reduced from the prototype shown e.g. to create heated sections of an assay flow channel. Multiple heaters on a single device could also be envisaged with various arrangements of sample chambers and/or flow paths. Nevertheless, the number of manufacturing steps required to provide heating and temperature control and functionality is just two.

Figure 9A:
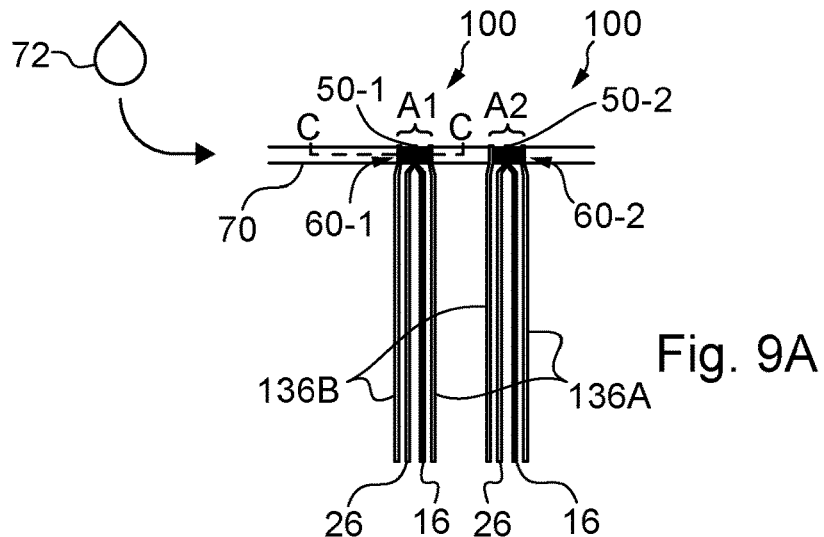
FIG. 9A shows a plan view of an example layout for a test sensor in which two successive, neighbouring sample areas, each having an integrated heater and thermocouple device 100, are provided within a single sample flow channel.
Figure 9B:
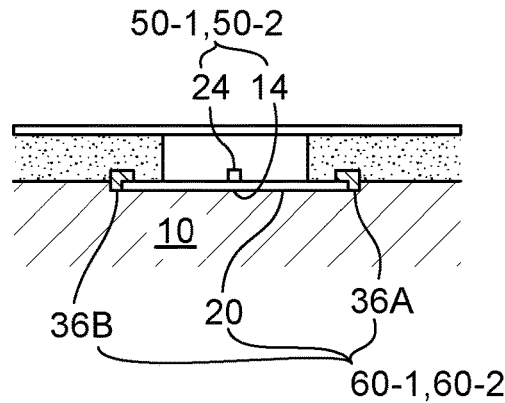
FIG. 9B shows a side cross-sectional view of one of the heating areas of FIG. 9A along line CC.

FIGS. 9A and 9B show plan and cross-section views of multiple, here two, heating areas within a single sample channel 70. Two sample areas A1 and A2 are provided overlaying respective resistive heater elements 20 between heater connector tracks 36A and 36B. Thus, two heaters 60-1 and 60-2 are provided in a single sample channel. Respective thermocouple junctions 50-1 and 50-2 are provided by narrow overlapping rectangular first and second thermocouple elements 14 and 24 preferably equi-spaced, and symmetrically centrally located with respect to respective connector members 36A and 36B. Sample fluids 72 may be drawn along the sample channel by capillary action and heated to a first temperature in sample area A1 where a first sample measurement may be made e.g. a photometric measurement before arriving in sample area A2 where the same measurement may be conducted at a different temperature. Other types of measurement that would benefit from the invention might include potentiometric, amperometric, conductimetric, impedimetric, optical, calorimetric, acoustic, and mechanical measurements, e.g. where it is desirable that temperature is well controlled.

Figure 10A:
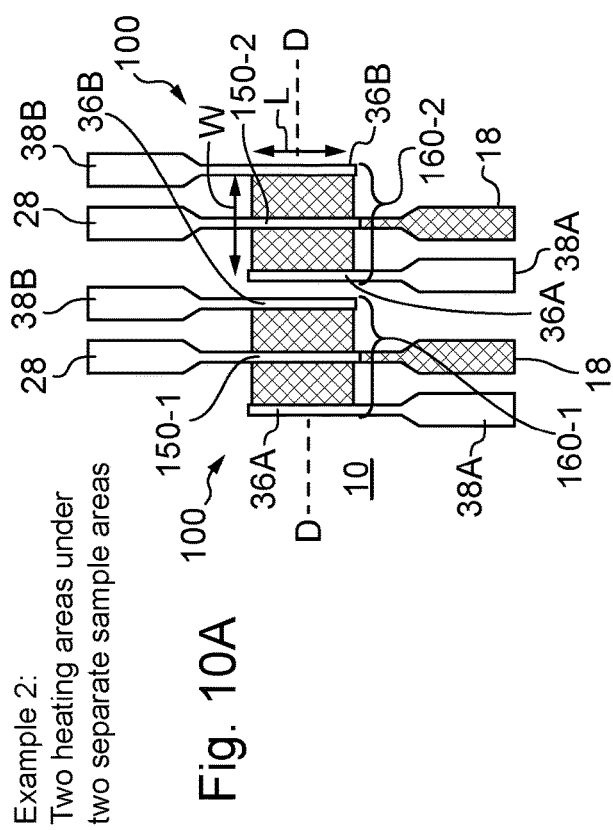
FIG. 10A shows a plan view of two separate heated sample areas each having an integrated heater and thermocouple 100. No sample containment features (such as an insulation layer 80) are shown for simplicity.
Figure 10B:
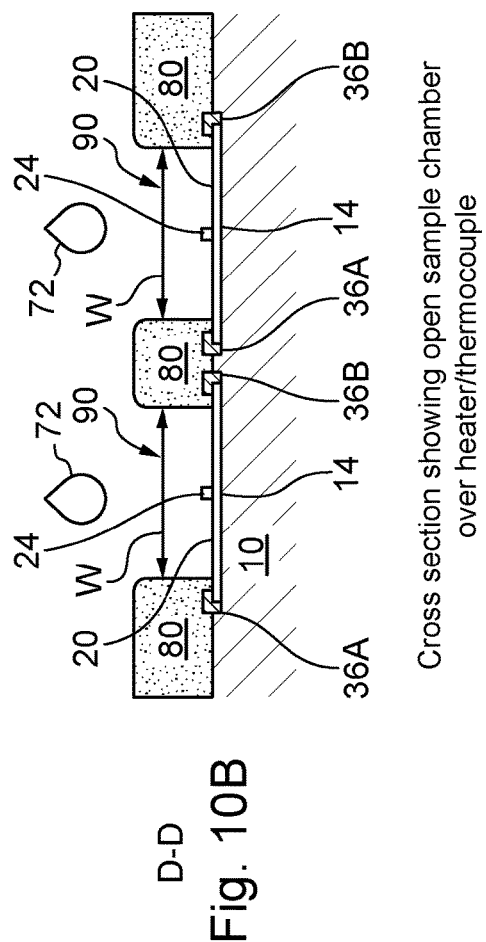
FIG. 10B shows a cross-sectional side elevation view of the two separated heated sample areas of FIG. 10A along line DD.

FIGS. 10A and 10B show two sample areas 90 defined by side walls of a thick spacer-type layer 80. For example, this may be formed from cut-outs in a film, or by wet or dry deposition techniques. The composition and/or thickness of this layer 80 will depend on the requirements of the application. The layer 80 may be used to separate one test area from another and/or to create a test well to hold more sample. Here, each area is heated by respective, resistive heating elements 20. Sample areas 90 have a width "W" defined by the separation between side walls of insulating layer 80 and a length "L" similarly defined. Typically, sample areas 90 are defined by respective apertures and side walls of insulation layer 80. Sample areas 90 are open and sample may be received into sample areas 90 from above. Each sample area 90 has a respective thermocouple junction 150-1, 150-2 and a respective heater 160-1, 160-2 formed from respective first and second thermocouple elements 14, 24 and respective resistive heater elements 20 and connector tracks 36A and 36B. The two sample areas 90 are entirely distinct and separate with no fluid connection from one to the other.

Figure 11A:
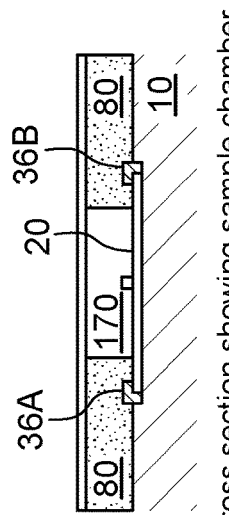
FIG. 11A shows a plan view of an example layout for a test sensor in which separate sample areas, having an integrated heater and thermocouple 100 in each of two separate side flow channels (leading from the same main flow channel).
Figure 11B:
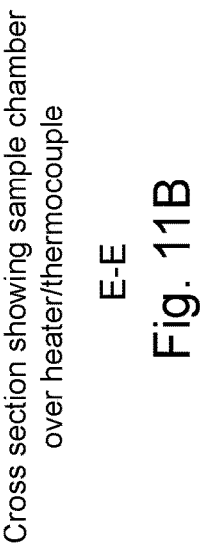
FIG. 11B shows a cross-sectional side elevation view of FIG. 11A along line EE.

FIGS. 11A and 11B show a sample channel 170 with two side channels (not labelled) for receiving sample fluid 72 from a main channel. Reservoirs 74 are typically capillary fill reservoirs which draw fluid along flow path 170 into and past heated sections 260-1 and 260-2 on each a respective side channel. Respective thermocouple junctions 250-1 and 250-2 enable, in effect, the same fluids to be heated to different temperatures before a measurement is taken or for a sample test to be repeated multiple times on (in effect) the same sample but under different or the same temperature conditions.

Figure 12A:
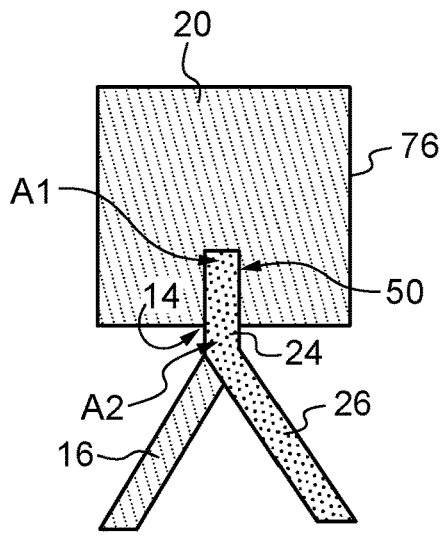
FIGS. 12A and 12B show plan views of the integrated heater and thermocouple device of the invention in an alternative embodiment. The heater connector tracks 36A, 36B are not shown for simplicity but examples of these are shown in FIGS. 2A, 2C, 3C and 10A at least.
Figure 12B:
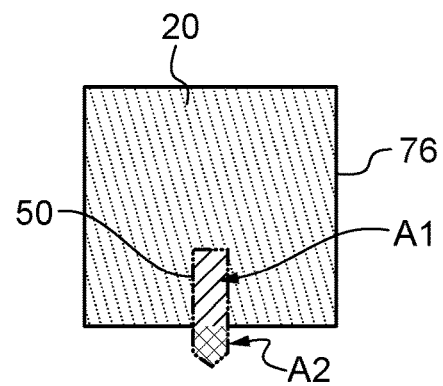

FIGS. 12A and 12B show a further embodiment in which a resistive heater element 20 and contiguous track portion leading to connector track 16 are overlaid by a second thermocouple element 24 (here shorter than the width of the resistive heater element 20) defining a first thermocouple element 14, part of which lies within the periphery 76 of first resistive element 20 and part of which lies beyond periphery 76 and comprises a portion of a track in the first layer leading to connector track 16. This can be seen more clearly in FIG. 12B where the portion of overlapping thermocouple element 14 within the periphery 76 of resistive heater element 20 is shown having an area A1 and the part outside periphery 76 is shown having an area A2. Thus, thermocouple junction 50 formed at the interface between first and second thermocouple elements 14 and 24 has a portion of area A1 which is heated and a portion of area A2 which is not heated by heater resistive element 20. This is not ideal and it is preferred that area A2 outside the heating element 20 is minimised. This is because the uneven heating/cooling in each of the first and second thermocouple elements 14, 24 may result. The measured temperature will be closely related to the temperature where the first and second thermocouple elements separate, which here may be slightly different to that on the actual resistive heater element 20 where the sample is to be heated. It will also be noted in this embodiment that the field lines near the terminal free end second thermocouple element 24, will no longer be uniform, again with possible uneven heating of each thermocouple element 14, 24 with respect to the other as a result.

Figure 13A:
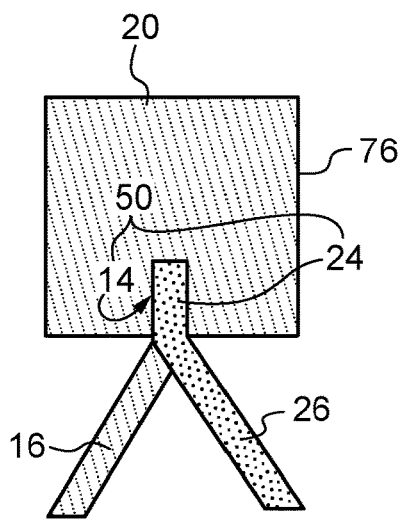
FIGS. 13A and 13B show plan views of the integrated heater and thermocouple device of the invention, in yet a further alternative embodiment, again heater connector tracks 36A, 36B are omitted.
Figure 13B:
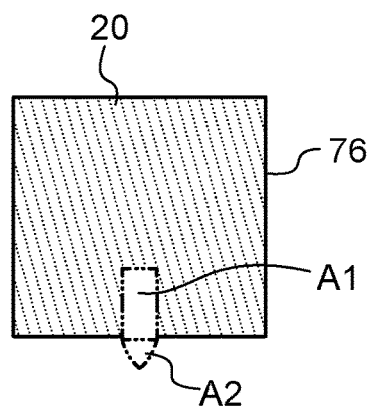

One way of achieving a small size of overlap area A2 is shown in FIGS. 13A and 13B. Here, thermocouple elements 14, 24 lead away from one another immediately at the periphery 76 of resistive heater element 20 providing a much smaller overlap A2 that lies outside periphery 76.

Figure 14A:
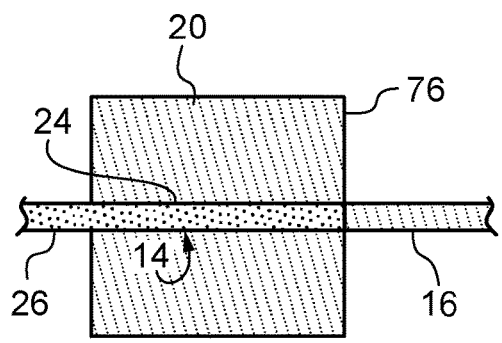
FIGS. 14A and 14B show plan views of the integrated heater and thermocouple device of the invention in a further alternative embodiment, again heater connector tracks 36A, 36B are omitted.
Figure 14B:
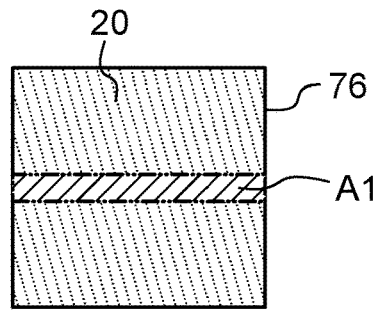

This may be further improved as shown in FIGS. 14A and 14B, in which connector tracks 16 and 26 each intersect the periphery 76 of resistive element 20 at opposing portions (edges) of the periphery. Thus, the area of the resistive heater element 20 overlapped by second thermocouple element 24 to form first thermocouple element 14 lies entirely within the periphery 76 (and here, for example, does not extend beyond the—here right hand side—of periphery 76) and there is minimal and typically near zero, overlap that does not lie within periphery 76 of resistive heater element 20. This, coupled with the shape of connector tracks 36A and 36B (not shown, but as in FIG. 2A) and the shape of resistive heater element 20 and the resulting uniform electric field extending between the connector tracks 36A and 36B, means that the entire resistive heater element 20 has the same resistance from connector track 36A to connector track 36B at each point along their respective length so that the current flowing and, therefore Joule heating will be comparable. This means that the resistance, and so resistive heating effect, across the sample area defined by resistive heating element 20 is generally or substantially uniform, particularly away from its periphery 76.

It is preferably to provide a uniform field (and so uniformly distributed field lines (across resistive heater element 20 so as to facilitate for (e.g. generally or substantially) even heating across heater element 20. The embodiments in FIGS. 1A to 2C, 9A to 11B, and 14A facilitate this by providing an elongate (here rectangular) second thermocouple element 24 along a line of equipotential with elongate edges parallel to opposing edges of tracks 36A and 36B.

There will be other configurations (physical arrangements) that could be envisaged from the teaching in this application that could be used to provide uniform electric field in further embodiments of the invention as would be understood by those skilled in the art.

However, FIGS. 3A to 3C and 12A to 13B and FIG. 15 facilitate provision of a uniform electric field across most of heater element 20 (typically at least 50% of the area of heater element 20) by providing a short overlap of second thermocouple element 24 on heater element 20. Some use a rectangular second thermocouple element 24 but this is not essential.

Figure 15:
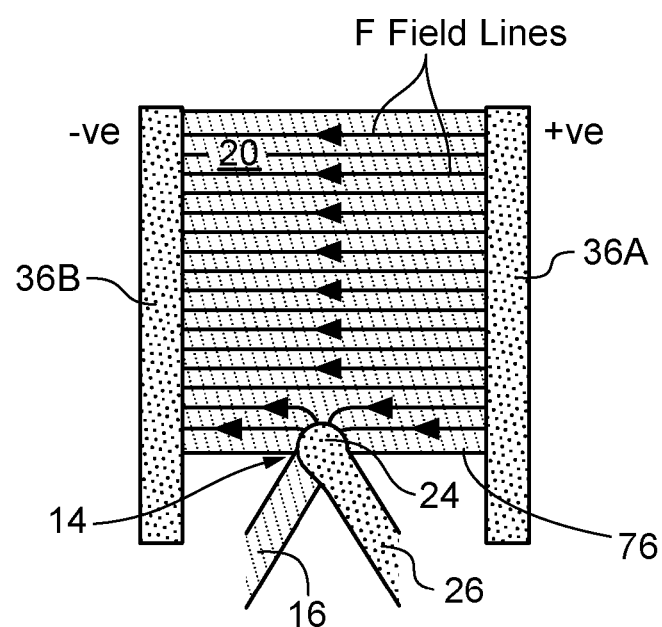
FIG. 15 shows a plan view of the integrated heater and thermocouple device of the invention in a further alternative embodiment, here heater connector tracks 36A, 36B are shown along with example field lines F.

In FIG. 15 a very short overlap of second thermocouple element 24 within the periphery 76 of heater element 20 is provided. Here, the thermocouple element has a distal free end with a rounded profile (here semi-circular). The resultant field lines are shown and are equispaced in around 80-90% of the area lying between connector tracks 36A, 36B indicating uniform electric field. Where rounded second thermocouple element 24 protrudes (overlaps) slightly onto the uppermost surface of heater element 20, the field lines F approach its rounded distal end in various orthogonal directions and the electric field is slightly perturbed in this region. The area of overlap of second thermocouple element 24 on resistive heater element may be small, ≤20%, or ≤10%, or ≤5% of the total area of resistive heater element, but it is preferably non-zero. Nevertheless, embodiments can be envisaged in which the second thermocouple element 24 touches a portion of a side wall of resistive heater element 20.

The material requirements for a heater element, using Joule effect, are for a (relatively) low resistance material for the connector tracks and a (relatively) high resistance material for the heater element itself. Typically, the tracks have a resistance of less than a few Ω whereas the heating element requires a resistance of around 100Ω or greater depending on the target temperature range and available voltage. Some other material properties may be dictated by the chosen lay down process.

The material requirements for a thermocouple element, using the Seebeck Effect are for the two materials forming the thermocouple with different Seebeck coefficient e.g. relative Seebeck coefficients of 5-65 µV/K, or 10-50 µV/K, or 10-25 µV/K, or 15 to 20 µV/K or 17 µV/K. For the thermoelectric effect to measure temperature, it is desirable to have two materials with Seebeck coefficients as different as possible.

In some embodiments, the choice of materials is more limited to those which can be used in test sensors, for a particular application, and/or to those usable in the desired manufacturing techniques.

For the two separate functions of heating and temperature measurement, it is necessary to have materials with charge mobility carriers, hence the selection of the materials is restricted to conductive and semi-conductive materials. Nevertheless, there remains a challenge in how these are to be used, so the high voltage required for the heater has low enough (or preferably minimal) effect on the thermocouple behaviour and performance to allow accurate temperature measurement. The present invention seeks to address these problem(s).

In our experiments, silver and carbon have been used but other materials can be used to increase the effects, for example, alternatively or in addition to silver, any one or more materials such as copper, gold, aluminium and nickel can be used for the highly conductive tracks while, alternatively or in addition to carbon, any one or more materials such as bismuth, constantan, silicon, germanium, antimony, iron, nichrome, molybdenum could be used for the heater element.

It is therefore theoretically possible to use the same materials for both the thermocouple and the heater but this still leaves the issue of the heater voltage being many times larger than the voltage signal needing to be measured from the thermocouple. Therefore as described elsewhere in this disclosure, arrangements have been shown to have the thermocouple output independent of the applied heater voltage without separating the heater element and thermocouple with an insulating layer. This enables not only the use of the same materials but also a reduction of lay down steps for the materials concerned.

For convenience, in our experiments we have used an electrically floated measuring system to detect the voltage changes in the thermocouple, but it is clear that if the use of electrically isolated power supplies and circuits is to be avoided, it would be possible to use a differential measurement by, for example, connecting the thermocouple to an instrumentation amplifier.

It has been found that if a specific geometry of the devices is used, combined with appropriate material selection, the number of different materials and lay down steps can be reduced to two:

1. Heater element and thermocouple material 1
2. Heater connector tracks and thermocouple material 2

The invention does not depend on the order of lay down of the two materials or the particular process used to lay down the materials.

Prototype Example

A prototype strip (see FIGS. 3A, 3B, and 3C) was built using screen printing as the material lay down method as follows:

Strip width is 10 mm. The outside silver tracks/contacts are the heater pad connectors and the middle silver and carbon tracks form a thermocouple on the heater pad.

The heater element reaches different temperatures depending on the voltage applied. The temperatures seen in the first prototype are a good match with the temperature range required for diagnostic assays including NATs.

A temperature dependent voltage can also be measured from the thermocouple that is unaffected by the voltage across the heater pad. The response times seen in FIG. 6 indicate that it is temperature not the voltage applied to the heater element that determines the thermocouple output.

To see if this could be used to control a stable on-strip temperature a test rig was built using an Arduino microcontroller to use the output from an off-the-shelf thermocouple amplifier (MAX31855 from adafruit.com) and run a "proportional-integral-derivative" (PID) control algorithm. The heater is powered from a 9V battery and controlled via one of the Arduino's PWM outputs to an optocoupler. The display shows the ambient temperature (Int.Temp) and a number derived from the strip thermocouple output (° C.) that was calibrated to reflect strip temperature. The required temperature is set in the Arduino software code. By taping a thermocouple to the strip surface and trying to get a good thermal connection with heat sink paste the temperature of the strip surface was measured while turning the control on and off (FIG. 7.). Strip heat up time is about 10 seconds from ambient temperature to just under 40° C. The on-board measurement/control is a big advantage over controlling a remote heater element and assuming good heat transfer or applying a voltage to a printed element and hoping it's the same each time.

Two further examples of integrated temperature control devices were built and tested. The heater/thermocouple designs tested are shown in FIGS. 16A and 16B. The heater/thermocouple were printed in a two layer print and a third insulation layer (not shown) printed over the heater/thermocouple to protect it from the sample fluid. The devices were built into a diagnostic test strip format by lamination with a spacer layer and lid film layer to form a capillary channel (e.g. similar to that shown in plan view in FIG. 9A (but with two heater/thermocouple devices rather than the one shown in each Figure here) and in cross section in FIG. 9B and photographed in FIG. 17).

In FIG. 16A, thermocouple element 24 is a small shaped disk or 'blob' of (here) silver ink, of nearly circular shape, connected to a slightly thinner connector track 26 leading away from it. This configuration helps to reduce and in some embodiments minimise the overlap outside the periphery of heater element 20.

Carbon connector track 16 connects to an extended connector track 116 of silver forming an 'additional' junction 51 that does not affect the measured thermocouple voltage as mentioned elsewhere. Similarly the contact pads 18, 128, 138A, 138B may be formed of both carbon and silver (here seen from underneath with carbon on an outermost exposed surface for robustness).

FIG. 16A shows an arrangement similar to that in FIG. 2A and 14A, save that here the contact tracks 16, 26 both leave from the same side of the periphery and lead away from each other (spreading out) so as to reduce any overlap lying outside the periphery of heater 20.

FIG. 17 shows a portion of a test sensor with a flow path 70 of relatively narrow width traversing (see vertical white lines) an e.g. square shaped heater 20 similar to that seen in FIG. 16B. The broad white band is an insulation layer defining the flow path and separating the fluid in flow path from the heater (and from the integrated thermocouple).

Figure 18:
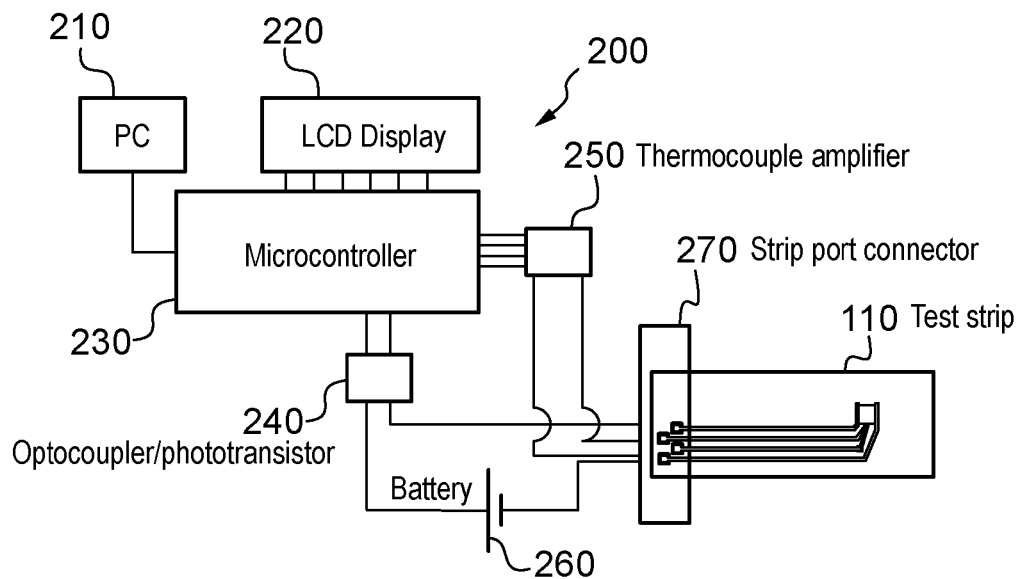
FIG. 18 shows a schematic control circuit for controlling, powering, and deriving measurements indicative of temperature, from a thermocouple on a test strip in an example embodiment.

FIG. 18 shows a schematic block diagram of a circuit 200 for controlling a test strip comprising a PC 210, an LCD display 220, a microcontroller 230 (e.g. Arduino Uno), an optocoupler/phototransistor 240 e.g. Vishay SFH618A, a thermocouple amplifier 250 (e.g. an Adafruit MAX31856 breakout) containing a 'cold' junction, a battery 260, a strip port connector 270 and a test sensor 110 (here a test strip) inserted in strip port connector 270.

Devices such as those shown in FIGS. 16A and 16B were tested in a test rig such as that seen in FIG. 18. The microcontroller 230 reads the input from the thermocouple amplifier 250 and outputs a voltage via pulse width modulation (PWM) to the phototransistor 240 which in turn controls the voltage applied to the test strip heater.

In a feedback control loop, the microcontroller 230 determines the thermocouple voltage (e.g. developed between the 'hot' thermocouple junction 50 and a 'cold' thermocouple junction inside the thermocouple amplifier 250) and as a result determines how much voltage to provide to the battery to maintain that temperature.

Figure 19:
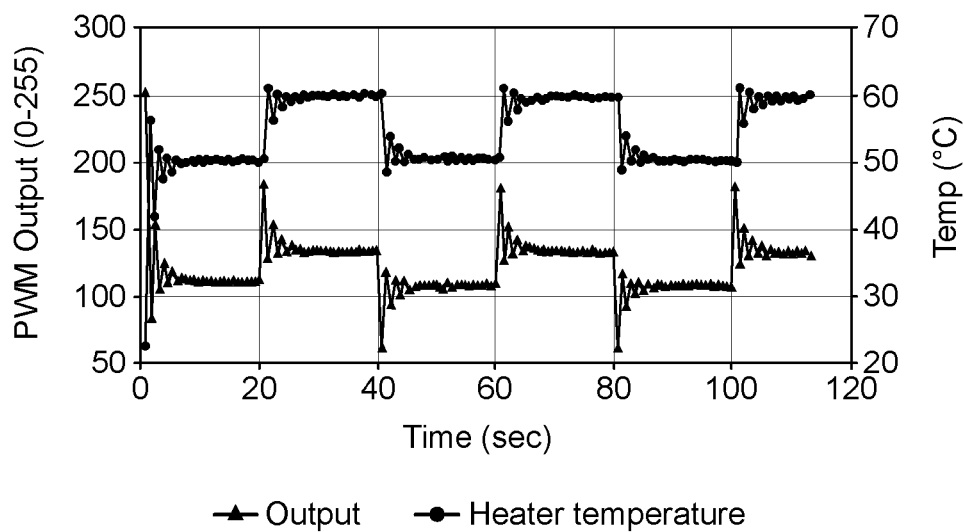
FIG. 19 shows a plot of pulse width modulator (PWM) output (indicative of the voltage applied to the resistive heater 20 and so heater temperature) and measured Temperature ° C. (indicated by a voltage measured between the 'hot' junction (thermocouple 50) and 'cold' remote junction) showing the variation with time when the heater is switched on and cycled between 50° C. and 60° C. at 20 second intervals.

The microcontroller 230 was used to program a temperature cycle between 50° C. and 60° C. at 20 second intervals using a device of the design shown in FIG. 16B. FIG. 19 shows a plot of the PWM Output and temperature of the heater with time. It can be seen that the heater 20 achieves the set temperature within about 10 seconds. The oscillation seen is indicative of the high sensitivity (in this example) of the heater 20 (which overshoots) to small changes in the voltage developed in the thermocouple 50 used to control it via the feedback loop.

Figure 20:
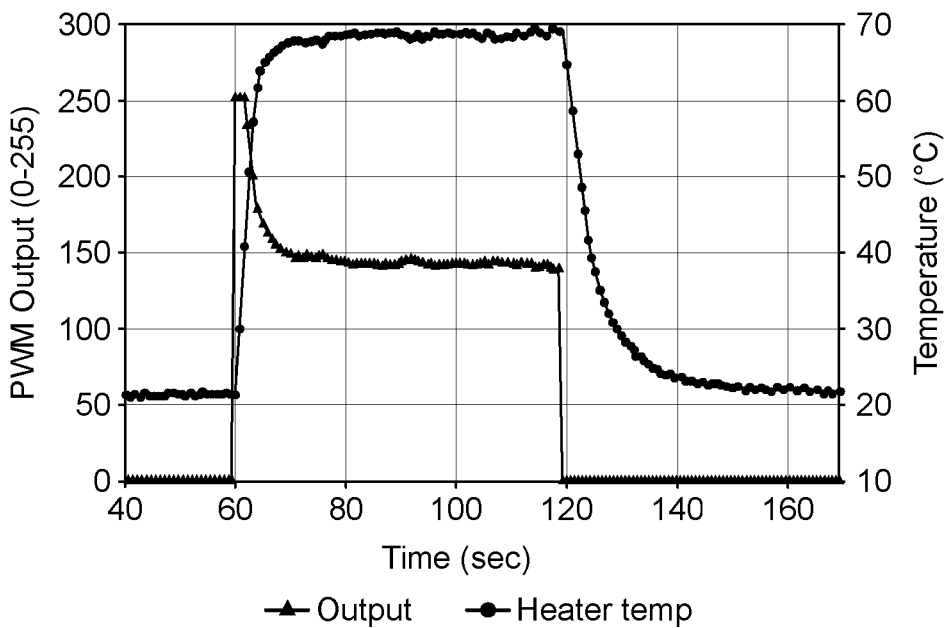
FIG. 20 is similar to FIG. 19, showing the heater 20 switch on and asked to reach a set point of 70° C., followed by a switch off after 60 seconds—a time period of 130 seconds (40 to 170 seconds) is shown.

A device of the design shown in FIG. 16B was filled with a liquid sample and the response to a setpoint of 70° C. for 1 minute recorded as shown in FIG. 20.

Figure 21:
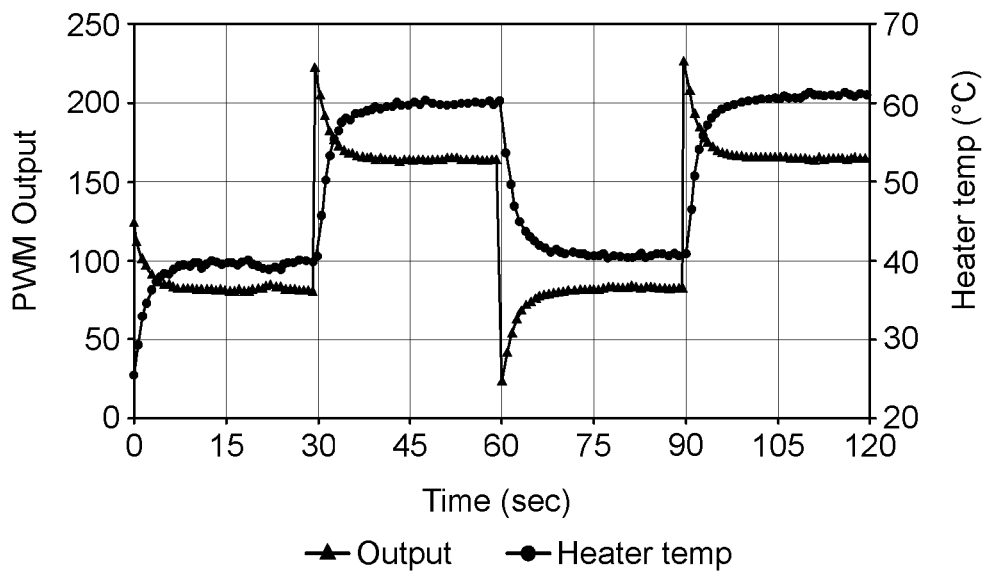
FIG. 21 is similar to FIG. 20 showing cycling between 40° C. and 60° C. at 30 second intervals.

A device with the heater/thermocouple design shown in FIG. 16A was built and a temperature cycle between 40° C. and 60° C. at 30 second intervals applied. FIG. 21 shows a plot of the PWM Output and temperature of the heater 20 with time. The absence of any oscillation compared to FIG. 19 is due to a modified control algorithm (reducing overshooting) rather than a difference in design between the devices.

Further embodiments will be apparent to those skilled in the art herein, all such alternative embodiments are intended to be covered by the claims. This is particularly the case where structural components may be of a different shape or size or construction but perform the purpose described herein or which may differ in shape and/or size and/or design elements but which, nevertheless, fulfil the purpose of the respective components described herein.

The invention claimed is:

1. A diagnostic test strip, comprising:
a substrate; and
an integrated resistive heater and thermocouple, the integrated resistive heater and thermocouple comprising:
a resistive heater, the resistive heater comprising:
a continuous layer of conductive material disposed in contact with the substrate, the continuous layer defining a periphery;
a first heater connector track in electrical communication with the continuous layer along a first portion of the periphery; and
a second heater connector track in electrical communication with the continuous layer along a second portion of the periphery, the first and second heater connector tracks being spaced apart from one another by the continuous layer of conductive material;
a thermocouple, the thermocouple comprising:
a thermocouple element configured such that the thermocouple element:
(i) underlies or overlies a portion of the continuous layer of conductive material and is in contact and disposed in electrical communication with the portion of the continuous layer of conductive material;
(ii) is disposed within the periphery of the continuous layer of conductive material between the first and second heater connector tracks; and
(iii) is formed of a conductive material having a conductivity higher than a conductivity of the conductive material of the continuous layer, wherein the thermocouple element and the portion of the continuous layer form a thermocouple junction therebetween;
a first thermocouple connector track in electrical communication with the portion of the continuous layer; and
a second thermocouple connector track in electrical communication with the thermocouple element;
wherein the first and second thermocouple connector tracks are separate and distinct from the first and second heater connector tracks.

2. A diagnostic test strip according to claim 1, wherein the resistive heater and first and second heater connector tracks are configured to provide a uniform electric field across at least part of the resistive heater.

3. A diagnostic test strip according to claim 1, wherein the thermocouple element is configured to enable a uniform electric field to be provided across at least part of the resistive heater in co-operation with one or both heater connector tracks.

4. A diagnostic test strip according to claim 3, wherein the thermocouple element has at least one edge parallel to a facing edge of one of the heater connector tracks.

5. A diagnostic test strip according to claim 1, wherein the first and second heater connecter tracks have facing edges which are parallel to one another.

6. A diagnostic test strip according to claim 1, wherein at least a portion of the thermocouple element is parallel to one or both of the heater connector tracks.

7. A diagnostic test strip according to claim 1, wherein the thermocouple element lies along a region of equipotential within the resistive heater.

8. A diagnostic test strip according to claim 1, wherein at least one of the thermocouple element or first thermocouple connector track intersect(s) a periphery of the resistive heater at a first location and at least one of the thermocouple element or second thermocouple connector track, intersect(s) the periphery at a second location, and wherein the first and second locations are at, at least one of, the same temperature, or the same potential.

9. A diagnostic test strip according to claim 1, wherein the thermocouple element lies substantially in between the first and second heater connector tracks.

10. A diagnostic test strip according to claim 1, wherein at least one of the thermocouple element or first or second heater connecter tracks is at least one of elongate, or rectangular.

11. A diagnostic test strip according to claim 1, wherein at least one of the resistive heater element, or the thermocouple element is configured so that the voltage indicative of temperature is substantially unaffected by the voltage applied to the resistive heater.

12. A diagnostic test strip according to claim 1, wherein a geometry of the continuous layer is arranged so that a field developed across the resistive heater is parallel to the uppermost surface of the thermocouple element.

13. A diagnostic test strip according to claim 12, wherein at least one of the thermocouple element, the first thermocouple connector track, the resistive heater, the second thermocouple connector track or the first or second heater connector tracks is planar.

14. A diagnostic test strip according to claim 1, wherein the resistive heater defines a heated test area.

15. A diagnostic test strip according to claim 1, further comprising: at least one of a sample chamber or a sample flowpath, and wherein the resistive heater is located adjacent to, or within, the sample chamber, or the flowpath.

16. A method of manufacturing a diagnostic test strip according to claim 1, comprising:
providing a substrate; and
providing on the substrate, an integrated resistive heater and thermocouple, the integrated resistive heater and thermocouple comprising:
a resistive heater, the resistive heater comprising:
a continuous layer of conductive material disposed in contact with the substrate, the continuous layer defining a periphery;
a first heater connector track in electrical communication with the continuous layer along a first portion of the periphery; and
a second heater connector track in electrical communication with the continuous layer along a second portion of the periphery, the first and second heater connector tracks being spaced apart from one another by the continuous layer of conductive material;
providing a thermocouple, the thermocouple comprising:
a thermocouple element configured such that the thermocouple element:
(i) underlies or overlies a portion of the continuous layer of conductive material and is in contact and disposed in electrical communication with the portion of the continuous layer of conductive material;
(ii) is disposed within the periphery of the continuous layer of conductive material between the first and second heater connector tracks; and
(iii) is formed of a conductive material having a conductivity higher than conductivity of the conductive material of the continuous layer, wherein the thermocouple element and the portion of the continuous layer form a thermocouple junction therebetween; and
providing
a first thermocouple connector track in electrical communication with the portion of the continuous layer; and
a second thermocouple connector track in electrical communication with the thermocouple element;
wherein the first and second thermocouple connector tracks are separate and distinct from the first and second heater connector tracks.

17. A method of conducting an assay, comprising:
providing a diagnostic test strip according to claim 1;
introducing a sample into a sample chamber and/or flowpath;
heating the sample using the resistive heater and thermocouple; and
making a measurement on the sample.

18. A method of conducting an assay according to claim 17, comprising at least one of:
allowing the sample to cool and repeating the measurement; and,
holding the sample at a predetermined temperature and repeating the measurement.

19. A diagnostic test strip according to claim 1, wherein the thermocouple element underlies or overlies the portion of the continuous layer of conductive material across the continuous layer from a first portion of the periphery to an opposing portion periphery, and does not overlie or under lie the heater connector tracks.

20. A diagnostic test strip according to claim 1, wherein the relative Seebeck coefficient of the material of the continuous layer to the material of the thermocouple element is within a range of 5-65 µV/K, 10-50 µV/K, 10-25 µV/K, 15 to 20 µV/K, or is 17 µV/K.

* * * * *